(12) United States Patent
Matsui et al.

(10) Patent No.: US 6,872,732 B2
(45) Date of Patent: Mar. 29, 2005

(54) HETEROCYCLIC DERIVATIVES AND MEDICINAL USE THEREOF

(75) Inventors: Hiroshi Matsui, Nara (JP); Hideo Kobayashi, Uji (JP); Satoru Azukizawa, Kyoto (JP); Masayasu Kasai, Kyoto (JP); Akihisa Yoshimi, Takatsuki (JP); Hiroaki Shirahase, Nagaokakyo (JP)

(73) Assignee: Kyoto Pharmaceutical Industries, Ltd., Kyoto (JP)

( * ) Notice: Subject to any disclaimer, the term of this patent is extended or adjusted under 35 U.S.C. 154(b) by 0 days.

(21) Appl. No.: 10/478,863

(22) PCT Filed: May 27, 2002

(86) PCT No.: PCT/JP02/05098
§ 371 (c)(1),
(2), (4) Date: Nov. 25, 2003

(87) PCT Pub. No.: WO02/096904
PCT Pub. Date: Dec. 5, 2002

(65) Prior Publication Data
US 2004/0180924 A1 Sep. 16, 2004

(30) Foreign Application Priority Data
May 29, 2001 (JP) .................. 2001-161488

(51) Int. Cl.[7] .................. A61K 31/47; C07D 401/12
(52) U.S. Cl. .................. 514/307; 546/147
(58) Field of Search .................. 514/307; 546/147

(56) References Cited

U.S. PATENT DOCUMENTS

| | | | | |
|---|---|---|---|---|
| 4,572,912 A | 2/1986 | Yoshioka et al. | ............ | 514/369 |
| 4,687,777 A | 8/1987 | Meguro et al. | ............ | 514/342 |
| 5,002,953 A | 3/1991 | Hindley | ............ | 514/275 |
| 6,121,282 A | * | 9/2000 | Dominianni et al. | ....... 514/307 |
| 6,589,963 B2 | * | 7/2003 | Matsui et al. | ....... 514/307 |

FOREIGN PATENT DOCUMENTS

| | | |
|---|---|---|
| WO | 93/23378 | 11/1993 |
| WO | 97/31907 | 9/1997 |
| WO | 98/00137 | 1/1998 |
| WO | 98/00403 | 1/1998 |
| WO | 01/40192 | 6/2001 |
| WO | 00/08002 | 2/2002 |
| WO | 02/12193 | 2/2002 |
| WO | 02/096880 | 12/2002 |

OTHER PUBLICATIONS

DATABASE XP–002239188, Bioorganic & Medicinal Chemistry, vol. 4, No. 1, 1994, pp. 57–62.
Heterocycles, 2001, vol. 55, No. 4, pp. 689–704.

* cited by examiner

*Primary Examiner*—D. Margaret Seaman
(74) *Attorney, Agent, or Firm*—Wenderoth, Lind & Ponack, L.L.P.

(57) ABSTRACT

The novel heterocyclic derivative of the present invention is a novel heterocyclic derivative having the formula (I')

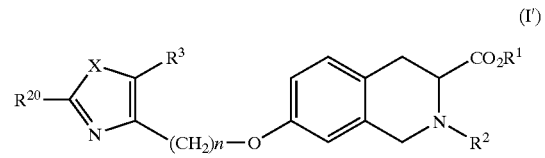

(I')

wherein $R^1$ is a hydrogen atom or $C_{1-6}$ alkyl, $R^2$ is —CO—$C(R^4)$=$C(R^4)$—$R^5$ wherein $R^4$ is a hydrogen atom or $C_{1-4}$ alkyl, and $R^5$ is $C_{4-8}$ alkyl, $C_{2-8}$ alkenyl, aryl or aromatic heterocycle, —CO—C≡C—$R^6$ wherein $R^6$ is $C_{1-8}$ alkyl and the like, $R^3$ is a hydrogen atom or $C_{1-4}$ alkyl, X is an oxygen atom or a sulfur atom, $R^{20}$ is optionally substituted phenyl, and n is an integer of 1 to 4, or a pharmaceutically acceptable salt thereof. The compound (I') of the present invention is useful as a hypoglycemic agent, a hypolipidemic agent, an insulin resistance improver, a therapeutic agent of diabetes, a therapeutic agent of diabetic complications, a glucose tolerance improver, an anti-arteriosclerosis agent, an anti-obesity agent, an antiinflammatory agent, an agent for the prophylaxis or treatment of PPAR-mediated diseases and an agent for the prophylaxis or treatment of syndrome X.

12 Claims, No Drawings

HETEROCYCLIC DERIVATIVES AND MEDICINAL USE THEREOF

This application is a U.S. National Stage of International Application No. PCT/JP02/05098, filed May 27, 2002.

TECHNICAL FIELD OF THE INVENTION

The present invention relates to a novel heterocyclic derivative and a pharmaceutically acceptable salt thereof, which have a hypoglycemic action, a blood hypolipidemic action, an insulin resistance-improving action and a PPAR (peroxisome proliferator-activated receptor)-activating action. The present invention also relates to a pharmaceutical composition comprising the above-mentioned novel heterocyclic derivative or a pharmaceutically acceptable salt thereof. Furthermore, the present invention relates to a hypoglycemic agent, a hypolipidemic agent, an insulin resistance improver, a therapeutic agent of diabetes, a therapeutic agent of diabetic complications, a glucose intolerance improver, an anti-atherosclerosis agent, an anti-obesity agent, an antiinflammatory agent, an agent for the prophylaxis or treatment of PPAR-mediated diseases and an agent for the prophylaxis or treatment of syndrome X, all of which comprising the above-mentioned novel heterocyclic derivative or a pharmaceutically acceptable salt thereof.

BACKGROUND OF THE INVENTION

As a therapeutic agent of diabetes, biguanide compounds having, as a main action, an inhibitory action on glucose absorption via the intestinal tract and on glucose release from the liver, sulfonylurea compounds having an accelerating action on insulin secretion as a main action, insulin and the like have been employed. However, biguanide compounds cause lactic acidosis, and sulfonylurea compounds sometimes cause serious hypoglycemia due to their strong hypoglycemic action. Therefore, a due care should be given when in use of these compounds. In recent years, there have been active researches and developments of a therapeutic agent of diabetes, which is free of these defects, with the consequence that various compounds having an insulin resistance-improving action have been found.

The insulin resistance plays an important role as a cause of non-insulin dependent diabetes mellitus (NIDDM), along with decrease in the insulin secretion. As an agent that improves insulin resistance, various thiazolidine compounds are known. Examples of such compound include 5-[4-[(6-hydroxy-2,5,7,8-tetramethylchroman-2-yl)methoxy] benzyl]-2,4-thiazolidinedione (general name: troglitazone) is described in U.S. Pat. No. 4,572,912 and EP0139421B1, 5-[[4-[2-(5-ethyl-pyridin-2-yl)ethoxy]phenyl]methyl]-2,4-thiazolidinedione (general name: pioglitazone) is described in U.S. Pat. No. 4,687,777 and EP0193256B1, and 5-[[4-[2-[N-methyl-N-(pyridin-2-yl)amino]ethoxy]phenyl] methyl]-2,4-thiazolidinedione (general name: rosiglitazone) is described in U.S. Pat. No. 5,002,953 and EP0306228B1. However, these pharmaceutical agents that improve insulin resistance may cause side effects such as hepatopathy, retention of fluid, edema, megalocardia; obesity and the like. Thus, the development of a highly safe insulin resistance improver effective for NIDDM has been desired.

SUMMARY OF THE INVENTION

It is therefore an object of the present invention to provide a compound having a hypoglycemic action, a blood hypolipidemic action, an insulin resistance-improving action and a PPAR activating action, which has a structure completely different from that of conventional compounds and which is highly safe, thereby to increase the diversity in and to broaden the range of selection from hypoglycemic agents, hypolipidemic agents, insulin resistance improvers, therapeutic agents of diabetes, therapeutic agents of diabetic complications, glucose intolerance improvers, anti-atherosclerosis agents, anti-obesity agents, antiinflammatory agents for the prophylaxis or treatment of PPAR-mediated diseases and agents for the prophylaxis or treatment of syndrome X.

The present inventors have conducted intensive studies in an attempt to solve the above-mentioned problems and found that a heterocyclic derivative having a novel structure of the formula (I')

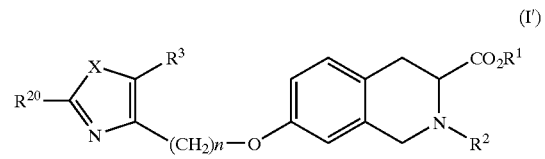

wherein
$R^1$ is a hydrogen atom or $C_{1-6}$ alkyl,
$R^2$ is —CO—C($R^4$)=C($R^4$)—$R^5$ wherein $R^4$ is a hydrogen atom or $C_{1-4}$ alkyl, and $R^5$ is $C_{4-8}$ alkyl, $C_{2-8}$ alkenyl, aryl or aromatic heterocycle, —CO—C≡C—$R^6$ wherein $R^6$ is $C_{1-8}$ alkyl, —CO—CO—$R^7$ wherein $R^7$ is $C_{1-8}$ alkyl or $C_{1-6}$ alkoxy, —N($R^8$)—CO—$R^9$ wherein $R^8$ is a hydrogen atom or $C_{1-4}$ alkyl, and $R^9$ is $C_{1-8}$ alkyl, $C_{1-8}$ alkoxy, aryl or aryl $C_{1-3}$ alkoxy, or aryl,
$R^3$ is a hydrogen atom or $C_{1-4}$ alkyl,
X is an oxygen atom or a sulfur atom,
$R^{20}$ is optionally substituted phenyl, and
n is an integer of 1 to 4,
and a pharmaceutically acceptable salt thereof have a hypoglycemic action, a blood hypolipidemic action, an insulin resistance-improving action and a PPAR activating action, as well as high safety.

Accordingly, the present invention provides the following.

(1) A novel heterocyclic derivative of the formula (I')

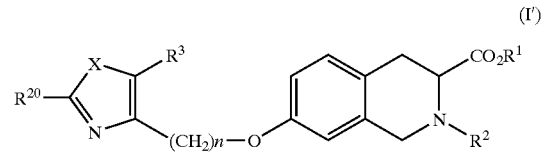

wherein
$R^1$ is a hydrogen atom or $C_{1-6}$ alkyl,
$R^2$ is —CO—C($R^4$)=C($R^4$)—$R^5$ wherein $R^4$ is a hydrogen atom or $C_{1-4}$ alkyl, and $R^5$ is $C_{4-8}$ alkyl, $C_{2-8}$ alkenyl, aryl or aromatic heterocycle, —CO—C≡C—$R^6$ wherein $R^6$ is $C_{1-8}$ alkyl, —CO—CO—$R^7$ wherein $R^7$ is $C_{1-8}$ alkyl or $C_{1-8}$ alkoxy, —N($R^8$)—CO—$R^9$ wherein $R^8$ is a hydrogen atom or $C_{1-4}$ alkyl, and $R^9$ is $C_{1-8}$ alkyl, $C_{1-8}$ alkoxy, aryl or aryl $C_{1-3}$ alkoxy, or aryl,
$R^3$ is a hydrogen atom or $C_{1-4}$ alkyl,
X is an oxygen atom or a sulfur atom,
$R^{20}$ is optionally substituted phenyl, and
n is an integer of 1 to 4,
or a pharmaceutically acceptable salt thereof.

(2) A novel heterocyclic derivative of the formula (I)

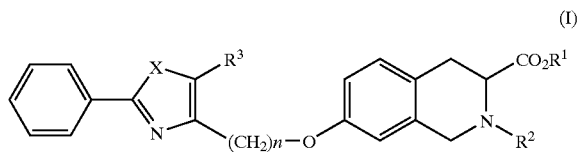

(I)

wherein
R$^1$ is a hydrogen atom or C$_{1-6}$ alkyl,
R$^2$ is —CO—C(R$^4$)=C(R$^4$)—R$^5$ wherein R$^4$ is a hydrogen atom or C$_{1-4}$ alkyl, and R$^5$ is C$_{4-8}$ alkyl, C$_{2-8}$ alkenyl, aryl or aromatic heterocycle, —CO—C≡C—R$^6$ wherein R$^6$ is C$_{1-8}$ alkyl, —CO—CO—R$^7$ wherein R$^7$ is C$_{1-8}$ alkyl or C$_{1-8}$ alkoxy, —N(R$^8$)—CO—R$^9$ wherein R$^8$ is a hydrogen atom or C$_{1-4}$ alkyl, and R$^9$ is C$_{1-8}$ alkyl, C$_{1-8}$ alkoxy, aryl or aryl C$_{1-3}$ alkoxy, or aryl,
R$^3$ is a hydrogen atom or C$_{1-4}$ alkyl,
X is an oxygen atom or a sulfur atom, and
n is an integer of 1 to 4,
or a pharmaceutically acceptable salt thereof.
(3) The novel heterocyclic derivative of the above-mentioned (2), wherein, in the formula (I), R$^1$ is a hydrogen atom, R$^3$ is a hydrogen atom or methyl, X is an oxygen atom, and n is 2, or a pharmaceutically acceptable salt thereof.
(4) The novel heterocyclic derivative of the above-mentioned (3), wherein, in the formula (I), R$^2$ is —CO—C(R$^4$)=C(R$^4$)-R$^5$ wherein R$^4$ is a hydrogen atom or C$_{1-4}$ alkyl and R$^5$ is C$_{4-8}$ alkyl, C$_{2-8}$ alkenyl or aryl, or a pharmaceutically acceptable salt thereof.
(5) The novel heterocyclic derivative of the above-mentioned (3), wherein, in the formula (I), R$^2$ is —CO—C≡C—R$^6$ wherein R$^6$ is C$_{1-8}$ alkyl, or a pharmaceutically acceptable salt thereof.
(6) The novel heterocyclic derivative of the above-mentioned (4), wherein, in the formula (I), R is —CO—C(R$^4$)=C(R$^4$)—R$^5$ wherein R$^4$ is a hydrogen atom and R$^5$ is C$_{4-8}$ alkyl or C$_{2-8}$ alkenyl, or a pharmaceutically acceptable salt thereof.
(7) The heterocyclic derivative of the above-mentioned (2), wherein the derivative of the formula (I) is any of the following [1] to [12], or a pharmaceutically acceptable salt thereof:
[1] 2-(2,4-hexadienoyl)-7-[2-(5-methyl-2-phenyloxazol-4-yl)ethoxy]-1,2,3,4-tetrahydroisoquinoline-(3S)-carboxylic acid,
[2] 2-(2-heptenoyl)-7-[2-(5-methyl-2-phenyloxazol-4-yl)ethoxy]-1,2,3,4-tetrahydroisoquinoline-(3S)-carboxylic acid,
[3] 7-[2-(5-methyl-2-phenyloxazol-4-yl)ethoxy]-2-(2,4-octadienoyl)-1,2,3,4-tetrahydroisoquinoline-(3S)-carboxylic acid,
[4] 2-(2-hexynoyl)-7-[2-(5-methyl-2-phenyloxazol-4-yl)ethoxy]-1,2,3,4-tetrahydroisoquinoline-(3S)-carboxylic acid,
[5] 2-cinnamoyl-7-[2-(5-methyl-2-phenyloxazol-4-yl)ethoxy]-1,2,3,4-tetrahydroisoquinoline-(3S)-carboxylic acid,
[6] 7-[2-(5-methyl-2-phenyloxazol-4-yl)ethoxy]-2-(2-oxobutyryl)-1,2,3,4-tetrahydroisoquinoline-(3S)-carboxylic acid,
[7] 2-ethoxyoxalyl-7-[2-(5-methyl-2-phenyloxazol-4-yl)ethoxy]-1,2,3,4-tetrahydroisoquinoline-(3S)-carboxylic acid,
[8] 7-[2-(5-methyl-2-phenyloxazol-4-yl)ethoxy]-2-(2-octenoyl)-1,2,3,4-tetrahydroisoquinoline-(3S)-carboxylic acid,

[9] 2-benzoylamino-7-[2-(5-methyl-2-phenyloxazol-4-yl)ethoxy]-1,2,3,4-tetrahydroisoquinoline-(3S)-carboxylic acid,
[10] 2-(2,2-dimethylpropionylamino)-7-[2-(5-methyl-2-phenyloxazol-4-yl)ethoxy]-1,2,3,4-tetrahydroisoquinoline-(3S)-carboxylic acid,
[11] 2-tert-butoxycarbonylamino-7-[2-(5-methyl-2-phenyloxazol-4-yl)ethoxy]-1,2,3,4-tetrahydroisoquinoline-(3S)-carboxylic 1 acid, and
[12] 7-[2-(5-methyl-2-phenyloxazol-4-yl)ethoxy]-2-phenyl-1,2,3,4-tetrahydroisoquinoline-(3RS)-carboxylic acid.
(8) A pharmaceutical composition containing the novel heterocyclic derivative of any of the above-mentioned (2) to (7) or a pharmaceutically acceptable salt thereof.
(9) A pharmaceutical agent-containing the novel heterocyclic derivative of any of the above-mentioned (2) to (7) or a pharmaceutically acceptable salt thereof, which is selected from the group consisting of a hypoglycemic agent, a hypolipidemic agent, an insulin resistance improver, a therapeutic agent of diabetes, a therapeutic agent of diabetic complications, a glucose intolerance improver, an anti-arteriosclerosis agent, an anti-obesity agent, an antiinflammatory agent, an agent for the prophylaxis or treatment of PPAR-mediated diseases and an agent for the prophylaxis or treatment of syndrome X.
(10) The heterocyclic derivative of the above-mentioned (1), wherein the derivative of the formula (I') is any of the following [13] to [29], or a pharmaceutically acceptable salt thereof:
[13] 7-{2-[2-(4-tert-butylphenyl)-5-methyloxazol-4-yl]ethoxy}-2-(2,4-hexadienoyl)-1,2,3,4-tetrahydroisoquinoline-(3S)-carboxylic acid,
[14] 2-(2,4-hexadienoyl)-7-{2-[5-methyl-2-(4-trifluoromethylphenyl)oxazol-4-yl]ethoxy}-1,2,3,4-tetrahydroisoquinoline-(3S)-carboxylic acid,
[15] 7-{2-[2-(4-fluorophenyl)-5-methyloxazol-4-yl]ethoxy}-2-(2,4-hexadienoyl)-1,2,3,4-tetrahydroisoquinoline-(3S)-carboxylic acid,
[16] 2-(2,4-hexadienoyl)-7-{2-[2-(4-methoxyphenyl)-5-methyloxazol-4-yl]ethoxy}-1,2,3,4-tetrahydroisoquinoline-(3S)-carboxylic acid,
[17] 2-(2,4-hexadienoyl)-7-{2-[5-methyl-2-(p-tolyl)oxazol-4-yl]ethoxy}-1,2,3,4-tetrahydroisoquinoline-(3S)-carboxylic acid,
[18] 7-{2-[2-(4-chlorophenyl)-5-methyloxazol-4-yl]ethoxy}-2-(2,4-hexadienoyl)-1,2,3,4-tetrahydroisoquinoline-(3S)-carboxylic acid,
[19] 7-{2-[2-(3,4-dimethoxyphenyl)-5-methyloxazol-4-yl]ethoxy}-2-(2,4-hexadienoyl)-1,2,3,4-tetrahydroisoquinoline-(3S)-carboxylic acid,
[20] 7-{2-[2-(3,4-methylenedioxyphenyl)-5-methyloxazol-4-yl]ethoxy}-2-(2,4-hexadienoyl)-1,2,3,4-tetrahydroisoquinoline-(3S)-carboxylic acid,
[21] 2-(2,4-hexadienoyl)-7-{2-[2-(4-hydroxyphenyl)-5-methyloxazol-4-yl]ethoxy}-1,2,3,4-tetrahydroisoquinoline-(3S)-carboxylic acid,
[22] 2-(2,4-hexadienoyl)-7-{2-[5-methyl-2-(o-tolyl)oxazol-4-yl]ethoxy}-1,2,3,4-tetrahydroisoquinoline-(3S)-carboxylic acid,
[23] 7-{2-[2-(4-benzyloxyphenyl)-5-methyloxazol-4-yl]ethoxy)-2-(2,4-hexadienoyl)-1,2,3,4-tetrahydroisoquinoline-(3S)-carboxylic acid,
[24] 2-(2,4-hexadienoyl)-7-{2-[2-(4-isopropylphenyl)-5-methyloxazol-4-yl]ethoxy}-1,2,3,4-tetrahydroisoquinoline-(3S)-carboxylic acid,
[25] 7-{2-[2-(2,4-dimethylphenyl)-5-methyloxazol-4-yl]ethoxy}-2-(2,4-hexadienoyl)-1,2,3,4-tetrahydroisoquinoline-(3S)-carboxylic acid,

[26] 2-(2,4-hexadienoyl)-7-(2-[5-methyl-2-(4-nitrophenyl)-oxazol-4-yl]ethoxy}-1,2,3,4-tetrahydroisoquinoline-(3S)-carboxylic acid,

[27] 7-{2-[2-(4-aminophenyl)-5-methyloxazol-4-yl]ethoxy}-2-(2,4-hexadienoyl)-1,2,3,4-tetrahydroisoquinoline-(3S)-carboxylic acid,

[28] 7-{2-[2-(4-dimethylaminophenyl)-5-methyloxazol-4-yl]ethoxy}-2-(2,4-hexadienoyl)-1,2,3,4-tetrahydroisoquinoline-(3S)-carboxylic acid, and

[29] 2-(2,4-hexadienoyl)-7-{2-[5-methyl-2-(2,4,6-trimethylphenyl)oxazol-4-yl]ethoxy}-1,2,3,4-tetrahydroisoquinoline-(3S)-carboxylic acid.

(11) A pharmaceutical composition containing the novel heterocyclic derivative of the above-mentioned (1) or (10) or a pharmaceutically acceptable salt thereof.

(12) A pharmaceutical agent containing the novel heterocyclic derivative of the above-mentioned (1) or (10) or a pharmaceutically acceptable salt thereof, which is selected from the group consisting of a hypoglycemic agent, a hypolipidemic agent, an insulin resistance improver, a therapeutic agent of diabetes, a therapeutic agent of diabetic complications, a glucose intolerance improver, an anti-arteriosclerosis agent, an anti-obesity agent, an antiinflammatory agent, an agent for the prophylaxis or treatment of PPAR-mediated diseases and an agent for the prophylaxis or treatment of syndrome X.

DETAILED DESCRIPTION OF THE INVENTION

Each symbol used in the present specification is explained in the following.

As the substituent for $R^{20}$, alkyl optionally substituted by fluorine atom, alkoxy, halogen, hydroxyl group, amino and nitro are exemplified.

As the aforementioned alkyl optionally substituted by fluorine atom, linear or branched chain alkyl having 1 to 6 carbon atoms is preferable. Examples thereof include methyl, ethyl, propyl, isopropyl, butyl, isobutyl, sec-butyl, tert-butyl, pentyl, isopentyl, neopentyl., hexyl, trifluoromethyl and the like, more preferably methyl, ethyl, propyl, isopropyl, tert-butyl and trifluoromethyl.

As the aforementioned alkoxy, $C_{1-4}$ alkoxy or aryl $C_{1-4}$ alkoxy is preferable. The $C_{1-4}$ alkoxy is a linear or branched chain alkoxy having 1 to 4 carbon atoms. It may have one oxygen, such as methoxy, ethoxy and propoxy, or two oxygens, such as methylenedioxy. The aryl $C_{1-4}$ alkoxy is that wherein the alkyl moiety is a linear or branched chain alkoxy having 1 to 4 carbon atoms and the aryl moiety is phenyl, naphthyl and the like. Examples thereof include benzyloxy, 1-naphthylmethoxy, 2-naphthylmethoxy, 1-phenylethoxy, 2-phenylethoxy, 1-naphthylethoxy, 2-naphthylethoxy, 2-(1-naphthyl)ethoxy, 3-phenylpropoxy, 3-(1-naphthyl)propoxy and the like, more preferably benzyloxy, 2-phenylethoxy and 3-phenylpropoxy.

As the aforementioned halogen, fluorine, chlorine, iodine and the like are mentioned. Preferred are fluorine and chlorine The aforementioned amino may be primary, secondary or tertiary. When amino is secondary or tertiary, the terminal alkyl is preferably a linear or branched chain alkyl having 1 to 4 carbon atoms, and the amino is more preferably —NH$_2$ and —N(CH$_3$)$_2$.

The number of substituent for $R^{20}$ is, for example, 0 to 4, preferably 0 to 3. As used herein, when the number of the substituent is 0, $R^{20}$ is unsubstituted phenyl.

Particularly preferably, $R^{20}$ is exemplified by phenyl, 4-tert-butylphenyl, 4-benzyloxyhenyl, 4-isopropylphenyl, 4-dimethylaminophenyl and the like.

The $C_{1-4}$ alkyl for $R^3$, $R^4$ and $R^8$ is a linear or branched chain alkyl having 1 to 4 carbon atoms, such as methyl, ethyl, propyl, isopropyl, butyl, isobutyl, sec-butyl, tert-butyl and the like, preferably methyl, ethyl, propyl and isopropyl.

The $C_{1-6}$ alkyl for $R^1$ is a linear or branched chain alkyl having 1 to 6 carbon atoms, such as methyl, ethyl, propyl, isopropyl, butyl, isobutyl, sec-butyl, tert-butyl, pentyl, isopentyl, neopentyl, hexyl and the like, preferably methyl, ethyl, propyl and tert-butyl.

The $C_{1-8}$ alkyl for $R^6$, $R^7$ and $R^9$ is a linear or branched chain alkyl having 1 to 8 carbon atoms, such as methyl, ethyl, propyl, isopropyl, butyl, isobutyl, sec-butyl, tert-butyl, pentyl, isopentyl, neopentyl, hexyl, heptyl, octyl and the like, preferably methyl, ethyl, propyl, tert-butyl, pentyl and hexyl.

The $C_{4-8}$ alkyl for $R^5$ is a linear or branched chain alkyl having 4 to 8-carbon atoms, such as butyl, isobutyl, sec-butyl, tert-butyl, pentyl, isopentyl, neopentyl, hexyl, heptyl, octyl and the like, preferably butyl, isobutyl, tert-butyl, pentyl and hexyl.

The $C_{2-8}$ alkenyl for $R^5$ is a linear or branched chain alkenyl having 2 to 8 carbon atoms, such as vinyl, 1-propenyl, 2-propenyl, isopropenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl and the like, preferably 1-propenyl, 1-butenyl, 1-pentenyl and 1-hexenyl.

As the aryl for $R^2$, $R^5$ and $R^9$, phenyl, naphthyl and the like, preferably phenyl, are exemplified.

As the aromatic heterocycle for $R^5$, a monocyclic hetero ring and fused hetero ring having at least one hetero atom selected from the group of oxygen atom, nitrogen atom and sulfur atom is preferable. The fused heterocycle in the present invention is a two ring system, which encompasses one having hetero atoms on both rings. Preferable monocyclic hetero ring is a 5- or 6-membered ring. The hetero ring constituting a preferable fused hetero ring is 5- or 6-membered hetero ring, and the ring without a hetero ring constituting a preferable fused heterocycle is a 5 or 6-membered ring. The aromatic hetero ring is, for example, a monocyclic hetero ring such as furyl, thienyl, pyridyl, imidazolyl, pyrazolyl, oxazolyl, isoxazolyl, thiazolyl, triazolyl, thiadiazolyl, oxadiazolyl, pyridazinyl, pyrimidinyl or pyrazinyl and the like; a fused hetero ring such as indolyl, isoindolyl, indolinyl, isoindolinyl, indazolyl, benzofuranyl, benzothiophenyl, benzoimidazolyl, benzoxazolyl, benzothiazolyl, quinolyl, isoquinolyl, benzoxazinyl, benzothiazinyl, furo[2,3-b]pyridyl, thieno[2,3-b]pyridyl, naphthyridinyl, imidazopyridyl, oxazolopyridyl, thiazolopyridyl and the like, which are preferably furyl, thienyl, pyridyl, oxazolyl, thiazolyl, indolyl, indolinyl, benzofuranyl, benzothiophenyl, quinolyl and isoquinolyl.

The aryl $C_{1-3}$ alkoxy for $R^9$ is, for example, that wherein the aryl moiety is preferably phenyl, naphthyl and the like, and the alkyl moiety is linear or branched chain alkoxy having 1 to 3 carbon atoms. Examples thereof include benzyloxy, 1-naphthylmethoxy, 2-naphthylmethoxy, 1-phenylethoxy, 2-phenylethoxy, 1-naphthylethoxy, 2-naphthylethoxy, 2-(1-naphthyl)ethoxy, 3-phenylpropoxy, 3-(1-naphthyl)propoxy and the like, preferably benzyloxy, 2-phenylethoxy and 3-phenylpropoxy.

The $C_{1-8}$ alkoxy for $R^7$ and $R^9$ is preferably linear or branched chain alkoxy having 1 to 8 carbon atoms, such as methoxy, ethoxy, propoxy, isopropoxy, butoxy, isobutoxy, sec-butoxy, tert-butoxy, pentyloxy, isopentyloxy, neopentyloxy, hexyloxy, heptyloxy, octyloxy and the like, preferably methoxy, ethoxy, propoxy, isopropoxy, butoxy, isobutoxy and tert-butoxy.

$R^1$ is preferably a hydrogen atom.

$R^2$ is preferably —CO—C($R^4$)=C($R^4$)—$R^5$ wherein $R^4$ is a hydrogen atom or $C_{1-4}$ alkyl, and $R^5$ is $C_{4-8}$ alkyl, $C_{2-8}$ alkenyl or aryl, or —CO—C≡C—$R^6$ wherein $R^6$ is $C_{1-8}$ alkyl. More preferably, $R^2$ is —CO—C($R^4$)=C($R^4$)—$R^5$ wherein $R^4$ is a hydrogen atom, and $R^5$ is $C_{4-8}$ alkyl or $C_{2-8}$ alkenyl.

$R^3$ is preferably a hydrogen atom or methyl.

X is preferably an oxygen atom.

n is preferably 2.

Preferable examples of the novel heterocyclic derivative of the formula (I) and a pharmaceutically acceptable salt thereof include (1) 2-(2,4-hexadienoyl)-7-[2-(5-methyl-2-phenyloxazol-4-yl)ethoxy]-1,2,3,4-tetrahydroisoquinoline-(3S)-carboxylic acid,
(2) 2-(2-heptenoyl)-7-[2-(5-methyl-2-phenyloxazol-4-yl)ethoxy]-1,2,3,4-tetrahydroisoquinoline-(3S)-carboxylic acid,
(3) 7-[2-(5-methyl-2-phenyloxazol-4-yl)ethoxy]-2-(2,4-octadienoyl)-1,2,3,4-tetrahydroisoquinoline-(3S)-carboxylic acid,
(4) 2-(2-hexynoyl)-7-[2-(5-methyl-2-phenyloxazol-4-yl)ethoxy]-1,2,3,4-tetrahydroisoquinoline-(3S)-carboxylic acid,
(5) 2-cinnamoyl-7-[2-(5-methyl-2-phenyloxazol-4-yl)ethoxy]-1,2,3,4-tetrahydroisoquinoline-(3S)-carboxylic acid,
(6) 7-[2-(5-methyl-2-phenyloxazol-4-yl)ethoxy]-2-(2-oxobutyryl)-1,2,3,4-tetrahydroisoquinoline-(3S)-carboxylic acid,
(7) 2-ethoxyoxalyl-7-[2-(5-methyl-2-phenyloxazol-4-yl)ethoxy]-1,2,3,4-tetrahydroisoquinoline-(3S)-carboxylic acid,
(8) 7-[2-(5-methyl-2-phenyloxazol-4-yl)ethoxy]-2-(2-octenoyl)-1,2,3,4-tetrahydroisoquinoline-(3S)-carboxylic acid,
(9) 2-benzoylamino-7-[2-(5-methyl-2-phenyloxazol-4-yl)ethoxy]-1,2,3,4-tetrahydroisoquinoline-(3S)-carboxylic acid,
(10) 2-(2,2-dimethylpropionylamino)-7-[2-(5-methyl-2-phenyloxazol-4-yl)ethoxy]-1,2,3,4-tetrahydroisoquinoline-(3S)-carboxylic acid,
(11) 2-tert-butoxycarbonylamino-7-[2-(5-methyl-2-phenyloxazol-4-yl)ethoxy]-1,2,3,4-tetrahydroisoquinoline-(3S)-carboxylic acid,
(12) 7-[2-(5-methyl-2-phenyloxazol-4-yl)ethoxy]-2-phenyl-1,2,3,4-tetrahydroisoquinoline-(3RS)-carboxylic acid,
(13) 7-{2-[2-(4-tert-butylphenyl)-5-methyloxazol-4-yl]ethoxy}-2-(2,4-hexadienoyl)-1,2,3,4-tetrahydroisoquinoline-(3S)-carboxylic acid,
(14) 2-(2,4-hexadienoyl)-7-{2-[5-methyl-2-(4-trifluoromethylphenyl)oxazol-4-yl]ethoxy}-1,2,3,4-tetrahydroisoquinoline-(3S)-carboxylic acid,
(15) 7-{2-[2-(4-fluorophenyl)-5-methyloxazol-4-yl]ethoxy}-2-(2,4-hexadienoyl)-1,2,3,4-tetrahydroisoquinoline-(3S)-carboxylic acid,
(16) 2-(2,4-hexadienoyl)-7-{2-[2-(4-methoxyphenyl)-5-methyloxazol-4-yl]ethoxy}-1,2,3,4-tetrahydroisoquinoline-(3S)-carboxylic acid,
(17) 2-(2,4-hexadienoyl)-7-{2-[5-methyl-2-(p-tolyl)oxazol-4-yl]ethoxy}-1,2,3,4-tetrahydroisoquinoline-(3S)-carboxylic acid,
(18) 7-{2-[2-(4-chlorophenyl)-5-methyloxazol-4-yl]ethoxy}-2-(2,4-hexadienoyl)-1,2,3,4-tetrahydroisoquinoline-(3S)-carboxylic acid,
(19) 7-{2-[2-(3,4-dimethoxyphenyl)-5-methyloxazol-4-yl]ethoxy}-2-(2,4-hexadienoyl)-1,2,3,4-tetrahydroisoquinoline-(3S)-carboxylic acid,
(20) 7-{2-[2-(3,4-methylenedioxyphenyl)-5-methyloxazol-4-yl]ethoxy}-2-(2,4-hexadienoyl)-1,2,3,4-tetrahydroisoquinoline-(3S)-carboxylic acid,
(21) 2-(2,4-hexadienoyl)-7-{2-[2-(4-hydroxyphenyl)-5-methyloxazol-4-yl]ethoxy}-1,2,3,4-tetrahydroisoquinoline-(3S)-carboxylic acid,
(22) 2-(2,4-hexadienoyl)-7-{2-[5-methyl-2-(o-tolyl)oxazol-4-yl]ethoxy}-1,2,3,4-tetrahydroisoquinoline-(3S)-carboxylic acid,
(23) 7-{2-[2-(4-benzyloxyphenyl)-5-methyloxazol-4-yl]ethoxy}-2-(2,4-hexadienoyl)-1,2,3,4-tetrahydroisoquinoline-(3S)-carboxylic acid,
(24) 2-(2,4-hexadienoyl)-7-{2-[2-(4-isopropylphenyl)-5-methyloxazol-4-yl]ethoxy}-1,2,3,4-tetrahydroisoquinoline-(3S)-carboxylic acid,
(25) 7-{2-[2-(2,4-dimethylphenyl)-5-methyloxazol-4-yl]ethoxy}-2-(2,4-hexadienoyl)-1,2,3,4-tetrahydroisoquinoline-(3S)-carboxylic acid,
(26) 2-(2,4-hexadienoyl)-7-{2-[5-methyl-2-(4-nitrophenyl)oxazol-4-yl]ethoxy}-1,2,3,4-tetrahydroisoquinoline-(3S)-carboxylic acid,
(27) 7-{2-[2-(4-aminophenyl)-5-methyloxazol-4-yl]ethoxy}-2-(2,4-hexadienoyl)-1,2,3,4-tetrahydroisoquinoline-(3S)-carboxylic acid,
(28) 7-{2-[2-(4-dimethylaminophenyl)-5-methyloxazol-4-yl]ethoxy}-2-(2,4-hexadienoyl)-1,2,3,4-tetrahydroisoquinoline-(3S)-carboxylic acid,
(29) 2-(2,4-hexadienoyl)-7-{2-[5-methyl-2-(2,4,6-trimethylphenyl)oxazol-4-yl]ethoxy}-1,2,3,4-tetrahydroisoquinoline-(3S)-carboxylic acid, and pharmaceutically acceptable salts thereof.

The heterocyclic derivative (I') comprises stereoisomers due to an asymmetric carbon at the 3-position carbon of 1,2,3,4-tetrahydroisoquinoline ring. The most preferable configuration is shown by the following formula (Ia)

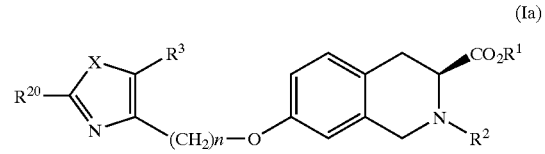

(Ia)

wherein $R^1$, $R^2$, $R^3$, $R^{20}$, X and n are as mentioned above.

When, in the formula (I'), $R^2$ is —CO—C($R^4$)=C($R^4$)—$R^5$ wherein $R^4$ and $R^5$ are as defined above, stereoisomers (cis form and trans form, or Z form and E form) are present at the double bond, both of which isomers are encompassed in the present invention.

The heterocyclic derivative (I') may form a pharmaceutically acceptable salt. When the heterocyclic derivative (I') has a basic group, an acid addition salt can be formed. The acid to form such acid addition salt is free of any particular limitation as long as it can form a salt with a basic moiety and is pharmaceutically acceptable. Examples of the acid include inorganic acids such as hydrochloric acid, sulfuric acid, phosphoric acid, nitric acid and the like, and organic acids such as oxalic acid, fumaric acid, maleic acid, citric acid, tartaric acid, methanesulfonic acid, toluenesulfonic acid and the like.

When the heterocyclic derivative (I') has an acidic group such as carboxyl group and the like, for example, alkali metal salts (e.g., sodium salt, potassium salt and the like), alkaline earth metal salts (e.g., calcium salt, magnesium salt and the like), organic base salts (e.g., triethylamine salt, dicyclohexylamine salt, pyridine salt, tert-butylamine salt and the like) and the like can be formed.

The heterocyclic derivative (I') of the present invention and a pharmaceutically acceptable salt thereof can be produced by any of the following production methods.

Production Method 1

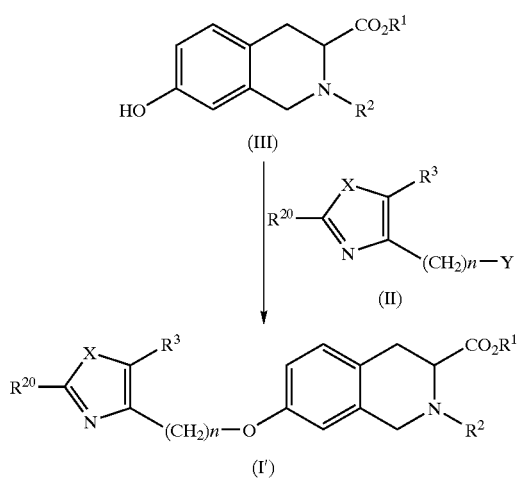

wherein $R^1$, $R^2$, $R^3$, $R^{20}$, X and n are as defined above, and Y is hydroxy or a leaving group such as halogen atom (fluorine atom, chlorine atom, bromine atom, iodine atom) or alkanesulfonyloxy (e.g., methanesulfonyloxy, ethanesulfonyloxy, propanesulfonyloxy, trifluoromethanesulfonyloxy and the like), arylsulfonyloxy (e.g., phenylsulfonyloxy and tolylsulfonyloxy and the like).

In Production Method 1, a compound having the formula (II) (compound (II)) and a compound having the formula (III) (compound (III)) are reacted to give a compound having the formula (I') (compound (I')).

Production Method 1-a: When Y is hydroxy group, Production Method 1 includes a dehydrating reaction such as Mitsunobu reaction (Reagents for Organic Synthesis by Fieser & Fieser, Vol. 6,645) and the like. The reaction generally proceeds in the presence of a solvent using an azo compound and a phosphine. Examples of the azo compound include azodicarboxylic acid di-$C_{1-4}$ alkyl (e.g., dimethyl azodicarboxylate, diethyl azodicarboxylate, diisopropyl azodicarboxylate and the like), azodicarboxamide (e.g., 1,1'-azobis(N,N'-dimethylformamide), 1,1'-(azodicarbonyl)dipiperidine and the like) and the like. Examples of the phosphine include triarylphosphine (e.g., triphenylphosphine and the like), tri($C_{1-8}$ alkyl)phosphine (e.g., tri-n-butylphosphine, tri-n-hexylphosphine, tri-n-octylphosphine and the like) and the like.

The solvent to be used in Production Method 1-a is free of any particular limitation as long as it is inert to the reaction. Examples thereof include dioxane, acetonitrile, tetrahydrofuran, chloroform, methylene chloride, ethylene chloride, benzene, toluene, xylene, ethyl acetate, N,N-dimethylformamide, N,N-dimethylacetamide, dimethyl sulfoxide and the like; and mixture of these and the like.

The amount of compound (II) to be used in Production Method 1-a is free of any particular limitation, and is generally 1–5 moles, preferably 1–3 moles, per 1 mole of compound (III). The amount of the azo compound and the phosphine to be used is generally 1–3 moles, preferably 1–1.5 moles, per 1 mole of compound (III).

While the reaction conditions in Production Method 1-a, such as reaction temperature, reaction time and the like vary depending on the reaction reagent, reaction solvent and the like to be used, the reaction is generally carried out at −30° C. to 50° C. for 30 min to about a dozen hours.

Production Method 1-b: When Y is a leaving group such as halogen atom or alkanesulfonyloxy (e.g., methanesulfonyloxy, ethanesulfonyloxy, propanesulfonyloxy, trifluoromethanesulfonyloxy and the like), arylsulfonyloxy (e.g., phenylsulfonyloxy, tolylsulfonyloxy and the like) and the like, Production Method 1-b is performed in a solvent similar to those used in Production Method 1-a in the presence of a base.

The base to be used in Production Method 1-b is free of any particular limitation, and is exemplified by inorganic bases such as alkali metal carbonates (e.g., sodium carbonate, sodium hydrogen carbonate, potassium carbonate, potassium bicarbonate and the like), alkali metal hydroxides (e.g., sodium hydroxide, potassium hydroxide and the like), metal hydride compounds (e.g., sodium hydride, potassium hydride, calcium hydride and the like) and the like; and organic bases such as alkali metal alcoholates (e.g., sodium methoxide, sodium ethoxide, potassium-t-butoxide and the like), amines (e.g., triethylamine, diisopropylethylamine and the like) and the like.

The amount of compound (II) to be used in Production Method 1-b is free of any particular limitation, and is generally 1–5 moles, preferably 1–3 moles, per 1 mole of compound (III). The amount of the base to be used is generally 1–5 moles, preferably 1–3 moles, per 1 mole of compound (III).

In Production Method 1-b, a catalyst can be used in a solvent in the presence of a base. Preferable solvent is toluene and the catalyst is exemplified by quaternary ammonium salts such as tetramethyl ammonium bromide, tetraethyl ammonium bromide, tetrabutyl ammonium bromide, tetraethyl ammonium chloride, tetraethyl ammonium fluoride, benzyltrimethyl ammonium bromide and the like, and tris[2-(2-methoxyethoxy)ethyl]amine. Preferably, tetraethylammonium fluoride or tris[2-(2-methoxyethoxy)ethyl]amine is used. The amount of catalyst to be used is generally 0.1–1 mole, preferably 0.1–0.5 mole, per 1 mole of compound (III).

While the reaction conditions in Production Method 1-b, such as reaction temperature, reaction time and the like vary depending on the reaction reagent, reaction solvent and the like to be used, the reaction is generally carried out at −30° C. to 150° C. for 30 min to about a dozen hours.

In Production Method 1-b, $R^1$ in compound (III) is preferably $C_{1-6}$ alkyl group. In this case, compound (I') wherein $R^1$ is $C_{1-6}$ alkyl group is obtained, which can be hydrolyzed by a method known per se to give compound (I') wherein $R^1$ is hydrogen atom.

The compound (III) can be produced by any of the following methods.

Production Method-a: In the formula (III), a compound having the formula (IIIb) (compound (IIIb)) wherein $R^2$ is —CO—C($R^4$)=C($R^4$)-$R^5$ wherein $R^4$ and $R^5$ are as defined above, —CO—C≡C—$R^6$ wherein $R^6$ is as defined above, or —CO—CO—$R^7$ wherein $R^7$ is as defined above, is produced.

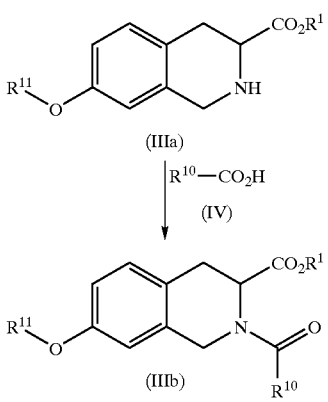

(IIIa)

↓ $R^{10}$—$CO_2H$ (IV)

(IIIb)

wherein $R^1$ is as defined above, $R^{10}$ is —C($R^4$)=C($R^4$)—$R^5$ wherein $R^4$ and $R^5$ are as defined above, —C≡C—$R^6$ wherein $R^6$ is as defined above, or —CO—$R^7$ wherein $R^7$ is as defined above, and $R^{11}$ is a hydrogen atom or a hydroxy-protecting group.

The hydroxy-protecting group for $R^{11}$ is exemplified by ethers such as methyl ether, isopropyl ether, tert-butyl ether, benzyl ether, allyl ether, methoxymethyl ether, tetrahydropyranyl ether, p-bromophenacyl ether, trimethylsilyl ether and the like, acetals, esters such as formyl, acetyl, monochloroacetyl, dichloroacetyl, trifluoroacetyl, methoxycarbonyl, ethoxycarbonyl, benzyloxycarbonyl, p-nitrobenzyloxycarbonyl, 2,2,2-trichloroethoxycarbonyl, benzoyl, methanesulfonyl, benzenesulfonyl, p-toluenesulfonyl and the like.

In Production Method-a, the compound (IV) is subjected to the reaction not only in the form of a free acid but also in the form of a salt (e.g., sodium, potassium, calcium, triethylamine, pyridine and the like), a reactive derivative (e.g., acid halide such as acid chloride, acid bromide and the like; acid anhydride; mixed acid anhydride with substituted phosphoric acid (e.g., dialkylphosphoric acid and the like), alkyl carbonate (e.g., monoethyl carbonate and the like), and the like; active amide which is an amide with imidazole and the like; esters such as cyanomethyl ester, 4-nitrophenyl ester and the like) and the like.

When compound (IV) is used in the form of a free acid or a salt in Production Method-a, the reaction is preferably carried out in the presence of a condensing agent. Examples of the condensing agent include dehydrating agents such as N,N'-disubstituted carbodiimides such as N,N'-dicyclohexylcarbodiimide and the like; carbodiimide compounds such as 1-ethyl-3-(3'-dimethylaminopropyl)carbodiimide, N-cyclohexyl-N'-morpholinoethylcarbodiimide, N-cyclohexyl-N'-(4-diethylaminocyclohexyl)carbodiimide and the like; azolide compounds (e.g., N,N'-carbonyldiimidazole, N,N'-thionyldiimidazole and the like) and the like. When these condensing agents are used, the reaction is considered to proceed via a reactive derivative of compound (IV).

In Production Method-a, the reaction between compound (IIIa) and compound (IV) is generally carried out in an inert solvent. Examples of the solvent include acetone, dioxane, acetonitrile, chloroform, benzene, methylene chloride, ethylene chloride, tetrahydrofuran, ethyl acetate, N,N-dimethylformamide, pyridine, water and the like, mixtures of these and the like. In addition, a base such as triethylamine, pyridine, 4-dimethylaminopyridine, potassium carbonate and the like can be used. When a base is used, the amount of the base to be used is generally 1–5 moles, preferably 1–3 moles, per 1 mole of compound (IIIa).

In Production Method-a, the amount of compound (IV) to be used is generally 1–5 moles, preferably 1–3 moles, per 1 mole of compound (IIIa).

While the reaction conditions of compound (IIIa) and compound (IV) in Production Method-a, such as reaction temperature, reaction time and the like vary depending on the reaction reagent, reaction solvent and the like to be used, the reaction is generally carried out at –30° C. to 150° C. for 30 min to about a dozen hours.

In Production Method-a, $R^{11}$ of compound (IIIa) is preferably a hydroxy-protecting group. In this case, a compound (IIIb) wherein $R^{11}$ is a hydroxy-protecting group is obtained, which is removed by a method known per se to give compound (IIIb) wherein $R^{11}$ is a hydrogen atom.

Production Method-b-1: A compound having the formula (IIId) (compound (IIId)) wherein, in the formula (III), $R^2$ is —N($R^8$)—CO—$R^9$ wherein $R^8$ is as defined above, and $R^9$ is $C_{1-8}$ alkyl or aryl, is produced.

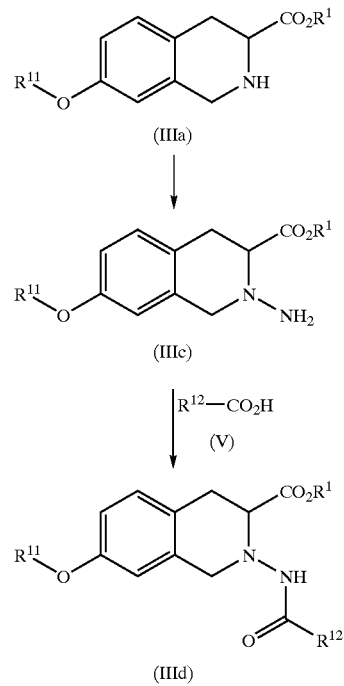

wherein $R^1$ and $R^{11}$ are as defined above, and $R^{12}$ is $C_{1-8}$ alkyl or aryl.

In Production Method-b-1, amino group is introduced into the 2-position of the 1,2,3,4-tetrahydroisoquinoline skeleton of compound (IIIa) to give a compound having the formula (IIIc) (compound (IIIc)), which is reacted with a compound having the formula (V) (compound (V)) to give a compound having the formula (IIId) (compound (IIId)).

The compound (IIIc) can be produced by a method known per se, such as reacting compound (IIIa) with chloramine, hydroxylamine-o-sulfonate, o-sulfonyl or o-acylhydroxylamine and the like, or reducing an N-nitroso form of compound (IIIa) and the like.

In Production Method-b-1, compound (IIIc) and compound (V) are reacted in the mode of reaction and reaction conditions similar to those of the reaction between compound (IIIa) and compound (IV) in Production Method-a.

Production Method-b-2: A compound having the formula (IIIe) (compound (IIIe)) wherein, in the formula (III), $R^2$ is —N(RB)—CO—$R^9$ wherein $R^8$ is as defined above, and $R^9$ is $C_{1-8}$ alkoxy or aryl $C_{1-3}$ alkoxy, is produced.

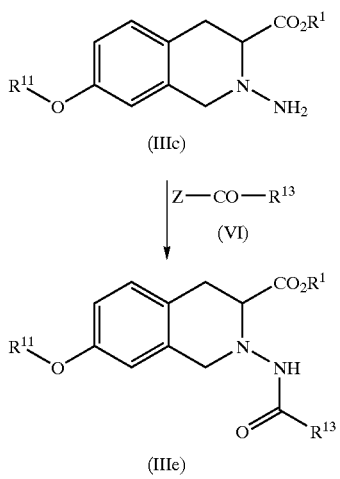

(IIIc)

↓ Z—CO—R$^{13}$ (VI)

(IIIe)

wherein R$^1$ and R$^{11}$ are as defined above, R$^{13}$ is C$_{1-8}$ alkoxy, aryl C$_{1-3}$ alkoxy, and Z is a halogen atom (fluorine atom, chlorine atom, bromine atom or iodine atom).

In Production Method-b-2, compound (IIIc) is reacted with a compound having the formula (VI) (compound (VI)) to give a compound having the formula (IIIe) (compound (IIIe)).

In Production Method-b-2, the reaction between compound (IIIc) and compound (VI) can be carried out in a solvent inert to the reaction in the presence of a base. Examples of the solvent include dioxane, acetonitrile, tetrahydrofuran, chloroform, methylene chloride, ethylene chloride, benzene, toluene, xylene, ethyl acetate, N,N-dimethylformamide, N,N-dimethylacetamide, dimethyl sulfoxide and the like, mixtures of these and the like.

The base to be used in Production Method-b-2 is free of any particular limitation, and is exemplified by inorganic bases such as alkali metal carbonates (e.g., sodium carbonate, sodium bicarbonate, potassium carbonate, potassium bicarbonate and the like), alkali metal hydroxides (e.g., sodium hydroxide, potassium hydroxide and the like) and the like; alkali metal alcoholates such as sodium methoxide, sodium ethoxide, potassium-t-butoxide and the like; metal hydride compounds such as sodium hydride, potassium hydride, calcium hydride and the like; and organic bases such as triethylamine, diisopropylethylamine and the like. The amount of the base to be used is generally 1–5 moles, preferably 1–3 moles, per 1 mole of compound (IIIc). The amount of compound (VI) to be used in Production Method-b-2 is generally 1–5 moles, preferably 1–3 moles, per 1 mole of compound (IIIc).

While the reaction conditions of compound (IIIc) and compound (VI) in Production Method-b-2, such as reaction temperature, reaction time and the like vary depending on the reaction reagent, reaction solvent and the like to be used, the reaction is generally carried out at −30° C. to 150° C. for 30 min to about a dozen hours.

In Production Method-b-1 and Production Method-b-2, R$^{11}$ of compound (IIIa) and compound (IIIc) is preferably a hydroxy-protecting group. In this case, a compound (IIId) and a compound (IIIe) wherein R$^{11}$ is a hydroxy-protecting group is obtained, which is removed by a method known per se to give a compound (IIId) and a compound (IIIe) wherein R$^{11}$ is a hydrogen atom.

Production Method 2

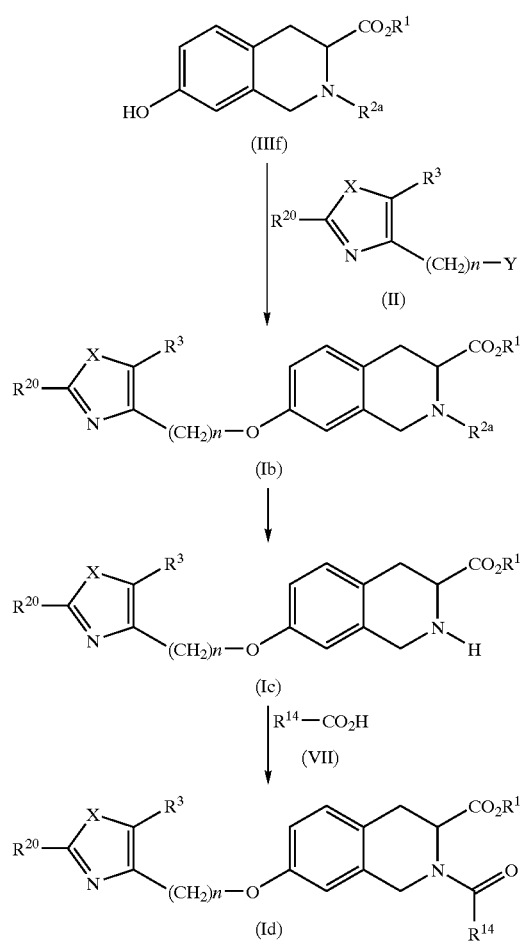

wherein R$^1$, R$^3$, R$^{20}$, X and n are as defined above, R$^{2a}$ is an amino-protecting group, and R$^{14}$ is —C(R$^4$)=C(R$^4$)—R$^5$ wherein R and R$^5$ are as defined above, —C≡C—R$^6$ wherein R$^6$ is as defined above, or —CO—R$^7$ wherein R$^7$ is as defined above.

The amino-protecting group for R$^{2a}$ is exemplified by formyl, monochloroacetyl, dichloroacetyl, trichloroacetyl, trifluoroacetyl, methoxycarbonyl, ethoxycarbonyl, benzyloxycarbonyl, p-nitrobenzyloxycarbonyl, diphenylmethyloxycarbonyl, methoxyymethylcarbonyl, methoxymethyloxycarbonyl, trimethylsilyl, 2,2,2-trichloroethoxycarbonyl, 2-methylsulfonylethyloxycarbonyl, t-butoxycarbonyl (hereinafter to be also referred to as Boc), trityl and the like.

In Production Method 2, the amino-protecting group of a compound having the formula (Ib) (compound (Ib)) is removed by a method known per se to give a compound having the formula (Ic) (compound (Ic)), which is reacted with a compound having the formula (VII) (compound (VII)) to give a compound having the formula (Id) (compound (Id)). The compound (Ib) can be produced by reacting compound (II) and a compound having the formula (IIIf) (compound (IIIf)) in the mode of reaction and reaction conditions similar to those of the reaction between compound (II) and compound (III) in Production Method 1.

In Production Method 2, the compound (VII) is subjected to the reaction not only in the form of a free acid but also in the form of a salt (e.g., salt of sodium, potassium, calcium, triethylamine, pyridine and the like), a reactive derivative (e.g., acid halide such as acid chloride, acid bromide and the like; acid anhydride; mixed acid anhydride with substituted phosphoric acid such as dialkylphosphoric acid and the like, with alkylcarbonate such as monoethyl carbonate and the like, and the like; active amide which is an amide with imidazole and the like; esters such as cyanomethyl ester, 4-nitrophenyl ester and the like) and the like.

When compound (VII) is used in the form of a free acid or a salt in Production Method 2, the reaction is preferably carried out in the presence of a condensing agent. Examples of the condensing agent include dehydrating agents such as N,N'-disubstituted carbodiimides (e.g., N,N'-dicyclohexylcarbodiimide and the like); carbodiimide compounds such as 1-ethyl-3-(3'-dimethylaminopropyl) carbodiimide, N-cyclohexyl-N'-morpholinoethylcarbodiimide, N-cyclohexyl-N'-(4-diethylaminocyclohexyl)carbodiimide and the like; azolide compounds (e.g., N,N'-carbonyldiimidazole, N,N'-thionyldiimidazole and the like) and the like; and the like. When these condensing agents are used, the reaction is considered to proceed via a reactive derivative of compound (VII).

In Production Method 2, the reaction between compound (Ic) and compound (VII) is generally carried out in an inert solvent. Examples of the solvent include acetone, dioxane, acetonitrile, chloroform, benzene, methylene chloride, ethylene chloride, tetrahydrofuran, ethyl acetate, N,N-dimethylformamide, pyridine, water and the like, mixtures of these and the like. In addition, a base such as triethylamine, pyridine, 4-dimethylaminopyridine, potassium carbonate and the like can be used. When a base is used, the amount of the base to be used is generally 1–5 moles, preferably 1–3 moles, per 1 mole of compound (Ic).

In Production Method 2, the amount of compound (VII) to be used is generally 1–5 moles, preferably 1–3 moles, per 1 mole of compound (Ic).

While the reaction conditions of compound (Ic) and compound (VII) in Production Method 2, such as reaction temperature, reaction time and the like vary depending on the reaction reagent, reaction solvent and the like to be used, the reaction is generally carried out at −30° C. to 150° C. for 30 min to about a dozen hours.

Production Method 3

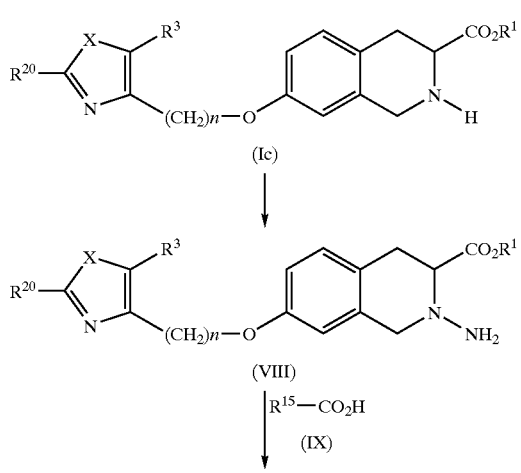

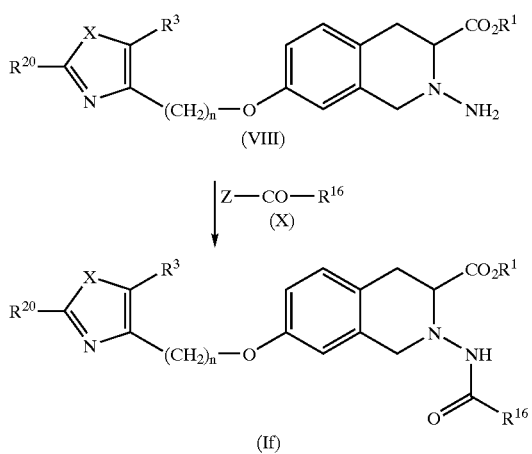

wherein $R^1$, $R^3$, $R^{20}$, X and n are as defined above, and $R^{15}$ is $C_{1-8}$ alkyl or aryl.

In Production Method 3, amino group is introduced into the 2-position of the 1,2,3,4-tetrahydroisoquinoline skeleton of compound (Ic) to give a compound having the formula (VIII) (compound (VIII)), which is reacted with a compound having the formula (IX) (compound (IX)) to give a compound having the formula (Ie) (compound (Ie)).

The compound (VIII) can be produced by a method known per se, such as reacting compound (Ic) with chloramine, hydroxylamine-o-sulfonate, o-sulfonyl or o-acylhydroxylamine and the like, or reducing an N-nitroso form of compound (Ic) and the like.

In Production Method 3, compound (VIII) and compound (IX) are reacted in the mode of reaction and reaction conditions similar to those of the reaction between compound (Ic) and compound (VII) in Production Method 2.

Production Method 4 wherein $R^1$, $R^3$, $R^{20}$, X and n are as defined above, $R^{16}$ is $C_{1-8}$ alkoxy or aryl $C_{1-3}$ alkoxy, and Z is a halogen atom (fluorine atom, chlorine atom, bromine atom or iodine atom).

In Production Method 4, compound (VIII) is reacted with a compound having the formula (X) (compound (X)) to give a compound having the formula (If) (compound (If)).

In Production Method 4, the reaction between compound (VIII) and compound (X) can be carried out in an inert solvent in the presence of a base. Examples of the solvent include dioxane, acetonitrile, tetrahydrofuran, chloroform, methylene chloride, ethylene chloride, benzene, toluene, xylene, ethyl acetate, N,N-dimethylformamide, N,N-dimethylacetamide, dimethyl sulfoxide and the like, mixtures of these and the like.

The base to be used in Production Method 4 is free of any particular limitation, and is exemplified by inorganic bases such as alkali metal carbonates (e.g., sodium carbonate, sodium bicarbonate, potassium carbonate, potassium bicarbonate and the like), alkali metal hydroxides (e.g., sodium hydroxide, potassium hydroxide and the like) and the like; alkali metal alcoholates such as sodium methoxide, sodium ethoxide, potassium-t-butoxide and the like; metal hydride compounds such as sodium hydride, potassium hydride, calcium hydride and the like; and organic bases such as triethylamine, diisopropylethylamine and the like. The amount of the base to be used is generally 1–5 moles, preferably 1–3 moles, per 1 mole of compound (VIII). The amount of compound (X) to be used in Production Method 4 is generally 1–5 moles, preferably 1–3 moles, per 1 mole of compound (VIII).

While the reaction conditions of compound (VIII) and compound (X) in Production Method 4, such as reaction temperature, reaction time and the like vary depending on the reaction reagent, reaction solvent and the like to be used, the reaction is generally carried out at −30° C. to 150° C. for 30 min to about a dozen hours.

The heterocyclic derivative (I') obtained in the above-mentioned Production Methods 1–4 may be isolated by a general method, and optionally purified by a general method such as recrystallization, preparative thin-layer chromatography, column chromatography and the like The heterocyclic derivative (I') may be converted to a pharmaceutically acceptable salt thereof by a method known per se.

The pharmaceutical composition comprising the heterocyclic derivative (I') or a pharmaceutically acceptable salt thereof of the present invention may contain an additive and the like. As an additive, exemplified are excipient (e.g., starch, lactose, sugar, calcium carbonate, calcium phosphate and the like), binder (e.g., starch, gum arabic, carboxymethylcellulose, hydroxypropylcellulose, crystalline cellulose and the like), lubricant (e.g., magnesium stearate, talc and the like), disintegrator (e.g., carboxymethylcellulose calcium, talc and the like), and the like.

The above-mentioned components are mixed to give a reparation for oral administration, such as capsule, tablet, powder, granule, dry syrup and the like, or a preparation for parenteral administration, such as injection, suppository and the like, according to a method known per se.

While the dose of the heterocyclic derivative (I') or a pharmaceutically acceptable salt thereof may vary according to the administration subject, symptom and other factors, when it is orally administered to an adult patient with, for example, diabetes, diabetic complication or hyperlipidemia, the single dose is approximately 1–500 mg, which is administered 1 to 3 times a day.

The heterocyclic derivative (I') and a pharmaceutically acceptable salt of the present invention show a superior hypoglycemic action, a blood hypolipidemic action, an insulin resistance-improving action and a PPAR activating action in mammals (e.g., human, horse, cattle, dog, cat, rat, mouse, hamster and the like), and are useful as a hypoglycemic agent, a hypolipidemic agent, an insulin resistance improver, a therapeutic agent of diabetes, a therapeutic agent of diabetic complication, a glucose intolerance improver, an anti-atherosclerosis agent, an anti-obesity agent, an antiinflammatory agent, an agent for the prophylaxis and treatment of PPAR-mediated disease and an agent for the prophylaxis and treatment of syndrome X. To be specific, the heterocyclic derivative (I') and a pharmaceutically acceptable salt of the present invention are useful for the prophylaxis and treatment of diabetes, diabetic complication, hyperlipidemia, atherosclerosis, hyperglycemia, diseases caused by insulin resistance glucose intolerance, diseases caused by insulin resistance, obesity, inflammation, PPAR-mediated disease and syndrome X.

The present invention is explained in more detail by Examples and Reference Examples, which are not to be construed as limitative.

EXAMPLE

Example 1 methyl 2-(2-heptenoyl)-7-[2-(5-methyl-2-phenyloxazol-4-yl)ethoxy]-1,2,3,4-tetrahydroisoquinoline-(3S)-carboxylate Methyl 2-(2-heptenoyl)-7-hydroxy-1,2,3,4-tetrahydroisoquinoline-(3S)-carboxylate (200 mg) and 2-(5-methyl-2-phenyloxazol-4-yl)ethyl methanesulfonate (355 mg) were dissolved in toluene (6 ml), and potassium carbonate (260 mg) and tetraethylammonium fluoride hydrate (40 mg) were added. The mixture was stirred at 80° C. for 10 h. Ethyl acetate (30 ml) was added to the reaction mixture, and the mixture was washed with water (30 ml) and saturated brine (20 ml), and dried ($Na_2SO_4$). The solvent was evaporated under reduced pressure and the obtained residue was purified by silica gel column chromatography to give the title compound (250 mg).

IR $_\nu$ (neat) cm$^{-1}$; 1740, 1661, 1622, 1506.
$^1$H-NMR (CDCl$_3$) δ (ppm); 0.92 (3H, br-t), 1.10–1.80 (4H, m) 1.80–2.40 (2H, m), 2.37 (3H, s), 2.96 (2H, t, J=6.6 Hz), 2.80–3.20 (2H, m), 3.59 (3H, s), 4.22 (2H, t, J=6.6 Hz), 4.50–5.60 (3H, m), 6.00–6.50 (1H, m), 6.60–7.20 (3H, m), 7.04 (1H, d, J=7.9 Hz), 7.30–7.60 (3H, m), 7.80–8.10 (2H, m).

Example 2

2-(2-heptenoyl)-7-[2-(5-methyl-2-phenyloxazol-4-yl) ethoxy]-1,2,3,4-tetrahydroisoquinoline-(3S)-carboxylic acid The compound (0.40 g) of Example 1 was dissolved in a mixture (9.5 ml) of tetrahydrofuran-methanol (3:1), and 1M aqueous lithium hydroxide solution (2.4 ml) was added. The mixture was stirred at 50° C. for 30 min. The reaction mixture was acidified with 10% aqueous citric acid solution, and the solution was concentrated under reduced pressure. The precipitated crystals were collected by filtration to give the title compound (0.36 g).

IR $_\nu$(Nujol) cm$^{-1}$; 1740, 1653, 1612, 1553, 1506.
$^1$H-NMR (CDCl$_3$) δ (ppm); 0.91 (3H, br-t), 1.10–1.75 (4H, m), 2.00–2.50 (2H, br), 2.32 (3H, s), 2.88 (2H, br-t), 2.90–3.30 (2H, m), 4.07 (2H, br-t), 4.50–5.10 (2H, m), 5.30–5.65 (1H, m), 6.30 (1H, d, J=14.9 Hz), 6.55–7.20 (3H, m), 7.04 (1H, d, J=7.9 Hz), 7.30–7.55 (3H, m), 7.70–8.05 (2H, m), 8.10–8.80 (1H, br).

Example 3

2-cinnamoyl-7-[2-(5-methyl-2-phenyloxazol-4-yl)ethoxy]-1,2,3,4-tetrahydroisoquinoline-(3S)-carboxylic acid (1) Methyl 2-tert-butoxycarbonyl-7-hydroxy-1,2,3,4-tetrahydroisoquinoline-(3S)-carboxylate (3.0 g) and 2-(5-methyl-2-phenyloxazol-4-yl)ethyl methanesulfonate (4.12 g) were dissolved in toluene (90 ml), and potassium carbonate (4.0 g) and tetraethylammonium fluoride hydrate (1.5 g) were added. The mixture was stirred at 80° C. for 5 h. The reaction mixture was washed with water (100 ml) and saturated brine (100 ml), and dried ($Na_2SO_4$). Toluene was evaporated under reduced pressure and the obtained residue was purified by silica gel column chromatography to give methyl 2-tert-butoxycarbonyl-7-[2-(5-methyl-2-phenyloxazol-4-yl)ethoxy]-1,2,3,4-tetrahydroisoquinoline-(3S)-carboxylate (4.49 g).
$^1$H-NMR (CDCl$_3$) δ (ppm); 1.46, 1.50 (9H, s, s), 2.36 (3H, s), 2.95 (2H, t, J=6.8 Hz), 2.90–3.30 (2H, m), 3.60 (3H, s), 4.21 (2H, t, J=6.8 Hz), 4.50, 4.60 (2H, s, s), 4.70–4.90, 5.00–5.20 (1H, m, m), 6.60–6.90 (2H, m), 7.12 (1H, d, J=8.4 Hz), 7.30–7.55 (3H, m), 7.90–8.15 (2H, m).

(2) The compound of (1) (14.0 g) was dissolved in formic acid (42 ml), and 8.78 M hydrogenchloride 2-propanol solution (10.7 ml) was added under ice-cooling. The mixture was stirred at room temperature for 20 min. To the reaction mixture were added ethyl acetate (300 ml) and water (500 ml), and the mixture was neutralized with sodium hydrogen carbonate, which was followed by separation of two layers. The obtained ethyl acetate layer was washed with saturated brine (500 ml) and dried ($Na_2SO_4$). Ethyl acetate was evaporated under reduced pressure and the obtained residue was purified by silica gel column chromatography to give methyl 7-[2-(5-methyl-2-phenyloxazol-4-yl)ethoxy]-1,2,3,4-tetrahydroisoquinoline-(3S)-carboxylate (9.4 g).

IR $_v$ (Nujol) cm$^{-1}$; 3560, 1744, 1643, 1612, 1578, 1553, 1504.

$^1$H-NMR (CDCl$_3$) δ (ppm); 1.92 (1H, s), 2.36 (3H, s), 2.80–3.20 (4H, m), 3.60–3.85 (1H, m), 3.76 (3H, s), 4.04 (2H, s), 4.21 (2H, t, J=6.6 Hz,), 6.57 (1H, d, J=2.0 Hz), 6.71 (1H, dd, J=2.0, 8.6 Hz), 7.00 (1H, d, J=8.6 Hz), 7.30–7.60 (3H, m), 7.85–8.15 (2H, m)

(3) The compound of (2) (0.4 g) was dissolved in methylene chloride (4 ml), and cinnamic acid (0.2 g) and 1-ethyl-3-(3'-dimethylaminopropyl)carbodiimide hydrochloride (0.29 g) were added. The mixture was stirred at room temperature for 1 h. Ethyl acetate (30 ml) was added, and the mixture was washed with 10% aqueous citric acid solution (15 ml) and saturated brine (15 ml), and dried ($Na_2SO_4$). The solvent was evaporated under reduced pressure, and the obtained residue was purified by silica gel column chromatography to give methyl 2-cinnamoyl-7-[2-(5-methyl-2-phenyloxazol-4-yl)ethoxy]-1,2,3,4-tetrahydroisoquinoline-(3S)-carboxylate (0.49 g).

IR $_v$ (Nujol) cm$^{-1}$; 1788, 1734, 1639, 1616.

$^1$H-NMR (CDCl$_3$) δ (ppm); 2.36 (3H, s), 2.96 (2H, t, J=6.4 Hz), 3.00–3.30 (2H, br), 3.61 (3H, s), 4.22 (2H, t, J=6.4 Hz), 4.60–5.65 (3H, m), 6.60–6.85 (2H, m), 6.97 (1H, d, J=15.1 Hz), 7.06 (1H, d, J=8.1 Hz), 7.25–8.75 (8H, m), 7.76 (1H, d, J=8.1 Hz), 7.85–8.10 (2H, m), 12.20–13.00 (1H, br).

(4) The compound of (3) (0.47 g) was dissolved in a mixture (11 ml) of tetrahydrofuran-methanol (3:1), and 1M aqueous lithium hydroxide solution (2.59 ml) was added. The mixture was stirred at 50° C. for 30 min and acidified with 10% aqueous citric acid solution. The solution was concentrated under reduced pressure and the precipitated crystals were collected by filtration to give the title compound (0.45 g).

IR $_v$ (Nujol) cm$^{-1}$; 1740, 1641, 1612, 1578, 1553, 1506.

$^1$H-NMR (DMSO-d$_6$) δ (ppm); 2.36 (3H, s), 2.75–3.25 (2H, br), 2.92 (2H, t, J=6.4 Hz), 4.20 (2H, t, J=6.4 Hz), 4.40–5.60 (3H, m), 6.70–6.95 (2H, m), 7.12 (1H, d, J=8.4 Hz), 7.30–8.10 (12H, m), 12.20–13.00 (1H, br).

Example 4

7-[2-(5-methyl-2-phenyloxazol-4-yl)ethoxy]-2-phenyl-1,2,3,4-tetrahydroisoquinoline-3-carboxylic acid (1) Ethyl 7-hydroxy-2-phenyl-1,2,3,4-tetrahydroisoquinoline-3-carboxylate (81 mg) was dissolved in toluene (2 ml), and 2-(5-methyl-2-phenyloxazol-4-yl)ethyl methanesulfonate (115 mg), potassium carbonate (112 mg) and tetraethylammonium fluoride hydrate (21 mg) were added. The mixture was stirred at 80° C. for 12 h. To the reaction mixture was added water (10 ml) and the mixture was extracted with ethyl acetate (20 ml), washed with saturated brine (20 ml), and dried ($Na_2SO_4$). The solvent was evaporated under reduced pressure, and the obtained residue was purified by column chromatography to give ethyl 7-[2-(5-methyl-2-phenyloxazol-4-yl)ethoxy]-2-phenyl-1,2,3,4-tetrahydroisoquinoline-3-carboxylate (87 mg).

$^1$H-NMR (CDCl$_3$) δ (ppm); 1.02 (3H, t, J=7.1 Hz), 2.37 (3H, s), 2.97 (2H, t, J=6.7 Hz), 3.23 (2H, d, J=4.1 Hz), 3.98 (2H, q, J=7.1 Hz), 4.24 (2H, t, J=6.7 Hz), 4.52 (2H, s), 4.74 (1H, t, J=4.1 Hz), 6.6–7.6 (11H, m), 7.8–8.1 (2H, m).

(2) The compound of (1) (87 mg) was dissolved in a mixture (2 ml) of tetrahydrofuran-methanol (3:1), and 1M aqueous lithium hydroxide solution (0.54 ml) was added. The mixture was stirred at 50° C. for 2 h and acidified with 10% aqueous citric acid solution. The solution was concentrated under reduced pressure and the precipitated crystals were collected by filtration to give the title compound (65 mg).

IR $_v$ (Nujol) cm$^{-1}$; 1717, 1599, 1504, 1460, 1377, 750, 718, 691.

$^1$H-NMR (CDCl$_3$) δ (ppm); 2.31 (3H, s), 2.88 (2H, t, J=6.3 Hz), 3.22 (2H, d, J=3.6 Hz), 4.09 (2H, t, J=6.3 Hz), 4.45 (2H, s), 4.68 (1H, t, J=3.6 Hz), 6.6–7.6 (11H, m), 7.8–8.1 (2H, m).

The following compounds were synthesized in the same manner as in Examples 1–4.

Example 5 methyl 2-(2,4-hexadienoyl)-7-[2-(5-methyl-2-phenyloxazol-4-yl)ethoxy]-1,2,3,4-tetrahydroisoquinoline-(3S)-carboxylate IR $_v$ (neat) cm$^{-1}$; 1740, 1653, 1626, 1601.

$^1$H-NMR (CDCl$_3$) δ (ppm); 1.85 (3H, d, J=5.1 Hz), 2.36 (3H, s), 2.96 (2H, t, J=6.8 Hz), 3.00–3.25 (2H, m), 3.59 (3H, s), 4.22 (2H, t, J=6.8 Hz), 4.50–5.60 (3H, m), 5.95–6.55 (3H, m), 6.60–6.85 (3H, m), 7.04 (1H, d, J=8.4 Hz), 7.15–7.35 (1H, m), 7.35–7.65 (3H, m), 7.80–8.15 (2H, m).

Example 6

2-(2,4-hexadienoyl)-7-[2-(5-methyl-2-phenyloxazol-4-yl)ethoxy]-1,2,3,4-tetrahydroisoquinoline-(3S)-carboxylic acid IR $_v$ (Nujol) cm$^{-1}$; 1738, 1651, 1616, 1545, 1506.

$^1$H-NMR (DMSO-d$_6$) δ (ppm); 1.82 (3H, d, J=4.4 Hz), 2.36 (3H, s), 2.75–3.25 (2H, br), 2.91 (2H, t, J=6.4 Hz), 4.19 (2H, t, J=6.4 Hz), 4.35–5.30 (3H, m), 6.00–6.70 (3H, m), 6.82 (2H, s), 6.90–7.30 (1H, m), 7.10 (1H, d, J=8.1 Hz), 7.35–7.65 (3H, m), 7.80–8.05 (2H, m), 12.20–13.30 (1H, br).

Example 7

7-[2-(5-methyl-2-phenyloxazol-4-yl)ethoxy]-2-(2,4-octadienoyl)-1,2,3,4-tetrahydroisoquinoline-(3S)-carboxylic acid IR $_v$ (Nujol) cm$^{-1}$; 1739, 1647, 1616, 1576, 1553.

$^1$H-NMR (DMSO-d$_6$) δ (ppm); 0.89 (3H, t, J=7.3 Hz), 1.42 (2H, m), 1.95–2.30 (2H, m), 2.35 (3H, s), 2.70–3.20 (2H, br), 2.91 (2H, t, J=6.6 Hz), 4.18 (2H, t, J=6.6 Hz), 4.40–5.30 (3H, m), 6.00–7.30 (5H, m) 6.81 (1H, s), 7.09 (1H, d, J=7.8 Hz), 7.35–7.65 (3H, m), 7.75–8.05 (2H, m).

Example 8

2-(2-hexynoyl)-7-[2-(5-methyl-2-phenyloxazol-4-yl)ethoxy]-1,2,3,4-tetrahydroisoquinoline-(3S)-carboxylic acid IR $_v$ (Nujol) cm$^{-1}$; 2235, 1732, 1634, 1583, 1553, 1506.

$^1$H-NMR (DMSO-d$_6$) δ (ppm); 0.95, 1.00 (3H, t,t, J=6.6 Hz), 1.30–1.75 (2H, m), 2.70–3.30 (4H, br), 2.91 (2H, t, J=6.6 Hz), 4.19 (2H, t, J=6.6 Hz), 4.40–5.30 (3H, m), 6.60–6.95 (2H, m), 7.11 (1H, d, J=7.9 Hz), 7.35–7.70 (3H, m), 7.80–8.05 (2H, m), 12.20–13.00 (1H, br).

Example 9

7-[2-(5-methyl-2-phenyloxazol-4-yl)ethoxy]-2-(2-oxo-butyryl)-1,2,3,4-tetrahydroisoquinoline-(3S)-carboxylic acid IR $_v$ (Nujol) cm$^{-1}$; 1743, 1719, 1623, 1605.

$^1$H-NMR (DMSO-d$_6$) δ (ppm); 1.01, 1.06 (3H, t, t, J=7.0 Hz), 2.35 (3H, s), 2.80 (2H, q, J=7.0 Hz), 2.91 (2H, t, J=6.4 Hz), 3.09 (2H, d, J=4.3 Hz), 4.18 (2H, t, J=6.4 Hz), 4.40–5.15 (3H, m), 6.65–6.90 (2H, m), 7.11 (1H, d, J=8.1 Hz), 7.35–7.65 (3H, m), 7.70–8.00 (2H, m).

Example 10

2-ethoxyoxalyl-7-[2-(5-methyl-2-phenyloxazol-4-yl)ethoxy]-1,2,3,4-tetrahydroisoquinoline-(3S)-carboxylic acid IR $_v$ (Nujol) cm$^{-1}$; 1738, 1661, 1614, 1587, 1553, 1504.

$^1$H-NMR (CDCl$_3$) δ (ppm); 1.28, 1.36 (3H, t, t, J=6.8 Hz), 2.32 (3H, s), 2.86 (2H, br-t), 2.95–3.40 (2H, m), 4.01 (2H, br-t), 4.37, 4.45 (2H, q, q, J=6.8 Hz), 4.60–5.10 (2H, m), 5.10–5.40 (1H, m), 6.40–6.80 (2H, m), 7.03 (1H, d, J=7.2 Hz), 7.30–7.55 (3H, m), 7.70–8.05 (3H, m).

Example 11

7-[2-(5-methyl-2-phenyloxazol-4-yl)ethoxy]-2-(2-octenoyl)-1,2,3,4-tetrahydroisoquinoline-(3S)-carboxylic acid IR $_v$ (Nujol) cm$^{-1}$; 1740, 1653, 1612, 1553, 1506.

$^1$H-NMR (CDCl$_3$) δ (ppm); 0.89 (3H, br-t), 1.10–1.75 (6H, m), 2.00–2.50 (2H, br-t), 2.32 (3H, s), 2.88 (2H, br-t), 2.95–3.40 (2H, m), 4.07 (2H, br-t), 4.50–5.10 (2H, m), 5.35–5.65 (1H, m), 6.31 (1H, d, J=14.8 Hz), 6.55–7.20 (3H, m), 7.04 (1H, d, J=7.9 Hz), 7.30–7.55 (3H, m), 7.70–8.05 (2H, m), 8.05–8.40 (1H, br).

Example 12

2-benzoylamino-7-[2-(5-methyl-2-phenyloxazol-4-yl)ethoxy]-1,2,3,4-tetrahydroisoquinoline-(3S)-carboxylic acid (1) The compound of Example 3 (2) (5 g) was dissolved in a mixture of 6M hydrochloric acid (20 ml) and methanol (15 ml), and sodium nitrite (2.2 g) was added by portions under ice-cooling. The mixture was stirred at room temperature for 15 h. Water (300 ml) was added, and the mixture was extracted with ethyl acetate (300 ml). The ethyl acetate layer was washed with saturated brine (100 ml), and dried (Na$_2$SO$_4$), and ethyl acetate was evaporated under reduced pressure. To the obtained crystalline residue was added isopropyl ether, and the mixture was filtrated to give methyl 7-[2-(5-methyl-2-phenyloxazol-4-yl)ethoxy]-2-nitroso-1,2,3,4-tetrahydroisoquinoline-(3S)-carboxylate as crystals (3.17 g).

IR $_v$ (Nujol) cm$^{-1}$; 1742, 1639, 1612, 1553, 1508.

$^1$H-NMR (CDCl$_3$) δ (ppm); 2.36 (3H, s), 2.96 (2H, t, J=6.6 Hz), 3.20–3.50 (2H, m), 3.62 (3H, s), 4.21 (2H, t, J=6.6 Hz), 4.50, 5.08 (2H, ABq, J=19.2 Hz), 5.80–6.00 (1H, m), 6.60–6.90 (2H, m) 7.08 (1H, d, J=8.3 Hz), 7.25–7.55 (3H, m), 7.80–8.10 (2H, m).

(2) The compound of (1) (3.15 g) was suspended in 50% acetic acid (30 ml) and zinc powder (1.95 g) was added. The mixture was stirred at 50° C. for 45 min and water (300 ml) was added. After neutralization with sodium hydrogen carbonate, ethyl acetate (500 ml) was added, and an insoluble material was filtered off. Two layers were separated and the ethyl acetate layer was washed with saturated brine (300 ml) and dried (Na$_2$SO$_4$). Ethyl acetate was evaporated under reduced pressure and the obtained residue was purified by silica gel column chromatography to give methyl 2-amino-7-[2-(5-methyl-2-phenyloxazol-4-yl)ethoxy]-1,2,3,4-tetrahydroisoquinoline-(3S)-carboxylate (1.88 g).

IR $_v$ (neat) cm$^{-1}$; 3342, 1738, 1641, 1614, 1555, 1504.

$^1$H-NMR (CDCl$_3$) δ (ppm); 2.36 (3H, s), 2.94 (2H, t, J=6.8 Hz), 2.95–3.20 (2H, m), 3.36 (2H, br-s), 3.60–3.90 (1H, m), 3.74 (3H, s), 3.95–4.35 (4H, m), 6.55 (1H, d, J=2.3 Hz), 6.71 (1H, dd, J=2.3, 8.4 Hz), 7.00 (1H, d, J=8.4 Hz), 7.20–7.60 (3H, m), 7.80–8.15 (2H, m).

(3) The compound of (2) (0.5 g) was dissolved in methylene chloride (5 ml), and triethylamine (0.22 ml) and benzoyl chloride (0.16 ml) were added under ice-cooling. The mixture was stirred at room temperature for 20 min and ethyl acetate (30 ml) was added. The mixture was washed with 10% aqueous citric acid solution (20 ml) and saturated brine (20 ml), and dried (Na$_2$SO$_4$). The solvent was evaporated under reduced pressure, and isopropyl ether was added to the obtained crystalline residue. Filtration gave methyl 2-benzoylamino-7-[2-(5-methyl-2-phenyloxazol-4-yl)ethoxy]-1,2,3,4-tetrahydroisoquinoline-(3S)-carboxylate as crystals (0.48 g).

IR $_v$ (Nujol) cm$^{-1}$; 3229, 1732, 1645, 1622, 1580, 1553, 1508.

$^1$H-NMR (CDCl$_3$) δ (ppm); 2.36 (3H, s), 2.95 (2H, t, J=6.8 Hz) 3.00–3.50 (2H, m), 3.66 (3H, s), 4.00–4.45 (5H, m), 6.55 (1H, d, J=2.3 Hz), 6.72 (1H, dd, J=2.3, 8.4 Hz), 7.01 (1H, d, J=8.4 Hz), 7.15–7.60 (6H, m), 7.60–7.80 (2H, m), 7.80–8.10 (2H, m), 8.21 (1H, br-s).

(4) The compound of (3) (0.45 g) was dissolved in a mixture (11 ml) of tetrahydrofuran-methanol (3:1), and 1M aqueous lithium hydroxide solution (2.64 ml) was added. The mixture was stirred at 50° C. for 30 min and acidified with 10% aqueous citric acid solution. The solution was concentrated under reduced pressure and the precipitated crystals were collected by filtration to give the title compound (0.36 g).

IR $_v$ (Nujol) cm$^{-1}$; 3258, 1761, 1713, 1639, 1612, 1580, 1555, 1502.

$^1$H-NMR (DMSO-d$_6$) δ (ppm); 2.34 (3H, s), 2.65–3.20 (4H, m), 3.80–4.50 (5H, m), 6.55–6.90 (2H, m), 7.06 (1H, d, J=8.6 Hz), 7.20–8.15 (10H, m), 9.77 (1H, br-s).

The following compounds were synthesized in the same manner as in Examples 1–4 and 12.

Example 13

2-(2,2-dimethylpropionylamino)-7-[2-(5-methyl-2-phenyloxazol-4-yl)ethoxy]-1,2,3,4-tetrahydroisoquinoline-(3S)-carboxylic acid IR $_v$ (Nujol) cm$^{-1}$; 3341, 1703, 1624, 1553, 1504.

$^1$H-NMR (CDCl$_3$) δ (ppm); 1.16 (9H, s), 2.35 (3H, s), 2.92 (2H, br-t), 2.95–3.20 (2H, m), 3.60–3.90 (1H, m), 4.04 (2H, br-s), 4.13 (2H, br-t), 6.59 (1H, br-s), 6.71 (1H, br-d), 7.02 (1H, d, J=8.4 Hz), 7.20–7.55 (3H, m), 7.70 (1H, br-s), 7.80–8.10 (2H, m), 8.50–10.20 (1H, br).

Example 14

2-tert-butoxycarbonylamino-7-[2-(5-methyl-2-phenyloxazol-4-yl)ethoxy]-1,2,3,4-tetrahydroisoquinoline-(3S)-carboxylic acid IR $_v$ (Nujol) cm$^{-1}$; 3350, 1715, 1645, 1614, 1553, 1504.

$^1$H-NMR (CDCl$_3$) δ (ppm); 1.45 (9H, s), 2.36 (3H, s), 2.90–3.40 (2H, m), 2.94 (2H, t, J=6.1 Hz), 4.08 (2H, br-s), 4.18 (2H, t, J=6.1 Hz), 6.25 (1H, br-s), 6.63 (1H, d, J=1.8 Hz), 6.75 (1H, dd, J=1.8, 8.6 Hz), 7.08 (1H, d, J=8.6 Hz), 7.30–7.55 (3H, m), 7.80–8.10 (2H, m).

Example 15
methyl 7-{2-[2-(4-tert-butylphenyl)-5-methyloxazol-4-yl]ethoxy}-2-(2,4-hexadienoyl)-1,2,3,4-tetrahydroisoquinoline-(3S)-carboxylate IR $_v$ (Nujol) cm$^{-1}$; 1744, 1653, 1626, 1603, 1504.

$^1$H-NMR (CDCl$_3$) δ (ppm); 1.33 (9H, s), 1.85 (3H, d, J=5.1 Hz), 2.35 (3H, s), 2.95 (2H, t, J=6.6 Hz), 3.05–3.25 (2H, m), 3.59 (3H, s), 4.20 (2H, t, J=6.6 Hz), 4.50–5.60 (3H, m), 6.05–6.45 (3H, m), 6.60–6.85 (2H, m), 7.04 (1H, d, J=8.1 Hz), 7.15–7.40 (1H, m), 7.43, 7.89 (4H, ABq, J=8.6 Hz).

Example 16
tert-butylamine 7-{2-[2-(4-tert-butylphenyl)-5-methyloxazol-4-yl]ethoxy}-2-(2,4-hexadienoyl)-1,2,3,4-tetrahydroisoquinoline-(3S)-carboxylate The compound of Example 15 (470 mg) was dissolved in a mixture (10 ml) of tetrahydrofuran-methanol (3:1), and 1M aqueous lithium hydroxide solution (2.6 ml) was added. The mixture was stirred at 50° C. for 30 min and acidified with 10% aqueous citric acid solution. The solution was concentrated under reduced pressure, and the precipitated crystals were collected by filtration. The obtained crystals were dissolved in ethyl ether (5 ml), and tert-butylamine (0.11 ml) and diisopropyl ether (20 ml) were added. The mixture was stirred at room temperature for 20 min and the precipitated crystals were collected by filtration to give the title compound (390 mg).

IR $_v$ (Nujol) cm$^{-1}$; 3396, 1651, 1634, 1558, 1506.

$^1$H-NMR (CDCl$_3$) δ (ppm); 0.97 (9H, s), 1.33 (9H, s), 1.65–1.95 (3H, m), 2.35 (3H, s), 2.80–3.20 (2H, m), 2.93 (2H, t, J=6.6 Hz), 4.16 (2H, t, J=6.6 Hz), 4.40–5.20 (3H, m), 5.95–6.45 (3H, m), 6.45–7.30 (7H, m), 7.42, 7.88 (4H, ABq, J=8.4 Hz).

The following compounds were synthesized in the same manner as in Examples 1–4 and 16.

Example 17
tert-butylamine 2-(2,4-hexadienoyl)-7-{2-[5-methyl-2-(4-trifluoromethylphenyl)oxazol-4-yl]ethoxy}-1,2,3,4-tetrahydroisoquinoline-(3S)-carboxylate IR $_v$ (Nujol) cm$^{-1}$; 2731, 2635, 2542, 1653, 1620, 1587, 1506.

$^1$H-NMR (CDCl$_3$) δ (ppm); 1.02 (9H, s), 1.60–2.10 (3H, m), 2.38 (3H, s), 2.65–3.40 (2H, m), 2.95 (2H, t, J=6.4 Hz), 4.17 (2H, t, J=6.4 Hz), 4.30–5.20 (3H, m), 5.60–7.35 (10H, m), 7.65, 8.06 (4H, ABq, J=8.4 Hz).

Example 18
tert-butylamine 7-{2-[2-(4-fluorophenyl)-5-methyloxazol-4-yl]ethoxy}-2-(2,4-hexadienoyl)-1,2,3,4-tetrahydroisoquinoline-(3S)-carboxylate IR $_v$ (Nujol) cm$^{-1}$; 3393, 2735, 2631, 2546, 1651, 1599, 1556.

$^1$H-NMR (CDCl$_3$) δ (ppm); 0.96 (9H, s), 1.83 (3H, br-d), 2.35 (3H, s), 2.80–3.30 (2H, m), 2.92 (2H, t, J=6.5 Hz), 4.16 (2H, t, J=6.5 Hz), 4.35–5.20 (3H, m), 5.94–6.41 (3H, m), 6.41–7.36 (9H, m), 7.80–8.10 (2H, m).

Example 19
tert-butylamine 2-(2,4-hexadienoyl)-7-{2-[2-(4-methoxyphenyl)-5-methyloxazol-4-yl]ethoxy}-1,2,3,4-tetrahydroisoquinoline-(3S)-carboxylate IR $_v$ (Nujol) cm$^{-1}$; 3393, 1651, 1616, 1585, 1556, 1501.

$^1$H-NMR (CDCl$_3$) δ (ppm); 0.98 (9H, s), 1.60–2.00 (3H, m), 2.33 (3H, s), 2.80–3.30 (2H, m), 2.92 (2H, t, J=6.6 Hz), 3.83 (3H, s), 4.15 (2H, t, J=6.6 Hz), 4.45–5.20 (3H, m), 5.80–6.40 (6H, m), 6.55–6.80 (2H, m), 6.85–7.00 (1H, m), 6.92, 7.89 (4H, ABq, J=9.0 Hz), 7.05–7.40 (1H, m).

Example 20
tert-butylamine 2-(2,4-hexadienoyl)-7-{2-[5-methyl-2-(p-tolyl)oxazol-4-yl]ethoxy}-1,2,3,4-tetrahydroisoquinoline-(3S)-carboxylate IR $_v$ (Nujol) cm$^{-1}$; 3348, 1652, 1622, 1558, 1504.

$^1$H-NMR (CDCl$_3$) δ (ppm); 1.01 (9H, s), 1.60–2.00 (3H, m), 2.35 (6H, s), 2.70–3.40 (4H, m), 4.16 (2H, br-t), 4.40–5.20 (2H, m), 5.60–6.45 (7H, m), 6.50–6.80 (2H, m), 6.85–7.20 (2H, m), 7.21, 7.85 (4H, ABq, J=8.1 Hz).

Example 21
tert-butylamine 7-{2-[2-(4-chlorophenyl)-5-methyloxazol-4-yl]ethoxy}-2-(2,4-hexadienoyl)-1,2,3,4-tetrahydroisoquinoline-(3S)-carboxylate IR $_v$ (Nujol) cm$^{-1}$; 3418, 2855, 2735, 2631, 2546, 1651, 1622, 1587.

$^1$H-NMR (CDCl$_3$) δ (ppm); 0.99 (9H, s), 1.84 (3H, d, J=4.9 Hz) 2.35 (3H, s), 2.93 (2H, t, J=6.6 Hz), 2.90–3.28 (2H, m), 4.16 (2H, t, J=6.6 Hz), 4.43–5.20 (3H, m), 5.50–6.10 (3H, br), 6.10–6.42 (3H, m), 6.51–6.77 (2H, m), 6.85–7.20 (2H, m), 7.37 (2H, d, J=8.6 Hz), 7.89 (2H, d).

Example 22
tert-butylamine 7-{2-[2-(3,4-dimethoxyphenyl)-5-methyloxazol-4-yl]ethoxy)-2-(2,4-hexadienoyl)-1,2,3,4-tetrahydroisoquinoline-(3S)-carboxylate IR $_v$ (Nujol) cm$^1$; 1651, 1626, 1556, 1504.

$^1$H-NMR (CDCl$_3$) δ (ppm); 1.00 (9H, s), 1.60–2.05 (3H, m), 2.35 (3H, s), 2.70–3.40 (4H, m,), 3.91, 3.94 (6H, s, s), 4.16 (2H, t, J=6.4 Hz), 4.45–5.20 (3H, m), 5.80–7.40 (11H, m), 7.40–7.70 (2H, m)

Example 23
tert-butylamine 7-{2-[2-(3,4-methylenedioxyphenyl)-5-methyloxazol-4-yl]ethoxy}-2-(2,4-hexadienoyl)-1,2,3,4-tetrahydroisoquinoline-(3S)-carboxylate IR $_v$ (Nujol) cm$^{-1}$; 3396, 1651, 1622, 1556, 1504.

$^1$H-NMR (CDCl$_3$) δ (ppm); 0.97. (9H, s), 1.86 (3H, m), 2.33 (3H, s), 2.80–3.25 (2H, m), 2.91 (2H, t, J=6.6 Hz), 4.15 (2H, t, J=6.6 Hz), 4.30–5.25 (1H, m), 5.98 (2H, s), 6.00–6.55 (3H, m-), 6.00–7.35 (8H, m), 7.40–7.65 (2H, m).

Example 24
tert-butylamine 2-(2,4-hexadienoyl)-7-{2-[2-(4-hydroxyphenyl)-5-methyloxazol-4-yl]ethoxy}-1,2,3,4-tetrahydroisoquinoline-(3S)-carboxylate IR $_v$ (Nujol) cm$^{-1}$; 3099, 2733, 2633, 2544, 1651, 1614, 1556.

$^1$H-NMR (DMSO-d$_6$+CDCl$_3$) δ (ppm); 1.11 (9H, s), 1.78 (3H, d, J=4.4 Hz), 2.29 (3H, s), 2.70–5.20 (13H, m), 5.97–6.52 (3H, m), 6.52–6.26 (6H, m), 7.69 (2H, d, J=8.3 Hz).

Example 25
tert-butylamine 2-(2,4-hexadienoyl)-7-(2-[5-methyl-2-(o-tolyl)oxazol-4-yl]ethoxy}-1,2,3,4-tetrahydroisoquinoline-(3S)-carboxylate IR $_v$ (Nujol) cm$^{-1}$; 1651, 1638, 1622, 1599, 1587, 1553, 1506.

$^1$H-NMR (DMSO-d$_6$) δ (ppm); 1.11 (9H, s), 1.70–1.90 (3H, br-d), 2.36 (3H, s), 2.61 (3H, s), 2.70–3.40 (2H, m), 2.91 (2H, t, J=6.3 Hz), 4.16 (2H, t, J=6.3 Hz), 4.40–5.20 (3H, m), 5.40–8.30 (3H, br), 5.90–6.80 (2H, m), 6.99 (1H, d, J=6.3 Hz), 7.15–7.50 (4H, m), 7.75–7.95 (1H, m).

Example 26
tert-butylamine 7-{2-[2-(4-benzyloxyphenyl)-5-methyloxazol-4-yl]ethoxy}-2-(2,4-hexadienoyl)-1,2,3,4-tetrahydroisoquinoline-(3S)-carboxylate IR $_v$ (Nujol) cm$^{-1}$; 1653, 1612, 1553.

$^1$H-NMR (CDCl$_3$) δ (ppm); 0.98 (9H, s), 1.65–1.95 (3H, m), 2.33 (3H, s), 2.80–3.40 (2H, m), 2.91 (2H, t, J=6.4 Hz), 4.16 (2H, t, J=6.4 Hz), 4.30–5.10 (2H, m), 5.60–6.45 (7H, m), 6.50–6.80 (2H, m), 6.85–7.10 (1H, m), 6.99, 7.89 (4H, ABq, J=8.8 Hz), 7.15–7.70 (6H, m).

Example 27
tert-butylamine 2-(2,4-hexadienoyl)-7-{2-[2-(4-isopropylphenyl)-5-methyloxazol-4-yl]ethoxy}-1,2,3,4-tetrahydroisoquinoline-(3S)-carboxylate IR $_v$ (Nujol) cm$^{-1}$; 3402, 1651, 1622, 1556, 1504.

$^1$H-NMR (CDCl$_3$) δ (ppm); 0.98 (9H, s), 1.26 (6H, d), 1.70–1.95 (3H, m), 2.34 (3H, s), 2.70–3.30 (3H, m), 2.93 (2H, t, =6.8 Hz), 4.16 (2H, t, J=6.8 Hz,), 4.40–5.30 (3H, m), 5.80–7.40 (10H, m), 7.26, 7.88 (4H, ABq, J=8.4 Hz).

Example 28
tert-butylamine 7-{2-[2-(2,4-dimethylphenyl)-5-methyloxazol-4-yl]ethoxy}-2-(2,4-hexadienoyl)-1,2,3,4-tetrahydroisoquinoline-(3S)-carboxylate IR $_v$ (Nujol) cm$^{-1}$; 2745, 2637, 2546, 1651, 1620, 1597, 1587, 1506.

$^1$H-NMR (CDCl$_3$) δ (ppm); 0.98 (9H, s), 1.60–1.95 (3H, m), 2.34 (6H, s), 2.60 (3H), 2.75–3.35 (2H, m), 2.93 (2H, t, J=6.6 Hz), 4.17 (2H, t, J=6.6 Hz), 4.40–5.25 (3H, m), 5.95–6.40 (3H, m), 6.40–7.40 (7H, m), 7.79 (1H, d, J=8.6 Hz).

Example 29
tert-butylamine 2-(2,4-hexadienoyl)-7-{2-[5-methyl-2-(4-nitrophenyl)oxazol-4-yl]ethoxy}-1,2,3,4-tetrahydroisoquinoline-(3S)-carboxylate IR $_v$ (Nujol) cm$^{-1}$; 3404, 2729, 2623, 2532, 1653, 1603, 1553, 1520.

$^1$H-NMR (CDCl$_3$) δ (ppm); 1.02 (9H, s), 1.83 (3H, d, J=4.1 Hz), 2.40 (3H, s), 2.96 (2H, t, J=6.1 Hz), 2.97–3.32 (2H, m), 4.18 (2H, t, J=6.1 Hz-), 4.41–5.18 (3H, m), 5.49–6.40 (6H, br), 6.50–6.80 (2H, m), 6.88–7.39 (2H, m), 8.09 (2H, d, J=9.0 Hz), 8.27 (2H, d, J=9.0 Hz).

Example 30
tert-butylamine 7-{2-[2-(4-aminophenyl)-5-methyloxazol-4-yl]ethoxy}-2-(2,4-hexadienoyl)-1,2,3,4-tetrahydroisoquinoline-(3S)-carboxylate IR $_v$ (Nujol) cm$^{-1}$; 3341, 3227, 2733, 2635, 2546, 1651, 1612, 1583, 1556, 1502.

$^1$H-NMR (CDCl$_3$-DMSO-d$_6$) δ (ppm); 1.03 (9H, s), 1.65–2.00 (3H, m), 2.32 (3H, s), 2.70–3.30 (2H, m), 2.89 (2H, t, J=6.6 Hz), 4.14 (2H, t, J=6.6 Hz), 4.30–5.80 (6H, m), 5.95–6.45 (3H, m), 6.45–7.45 (6H, m), 7.72 (2H, ABq, J=8.4 Hz).

Example 31
tert-butylamine 7-{2-[2-(4-dimethylaminophenyl)-5-methyloxazol-4-yl]ethoxy}-2-(2,4-hexadienoyl)-1,2,3,4-tetrahydroisoquinoline-(3S)-carboxylate IR $_v$ (Nujol) cm$^{-1}$; 3398, 2741, 2635, 2548, 1651, 1614, 1556.

$^1$H-NMR (CDCl$_3$) δ (ppm); 1.00 (9H, s), 1.84 (3H, d, J=5.3 Hz), 2.32 (3H, s), 2.70–3.38 (4H, m), 2.99 (6H, s), 4.15 (2H, t, J=6.7 Hz), 4.30–5.16 (3H, m), 5.47–6.45 (6H, m), 6.53–7.40 (8H, m), 7.82 (2H, d, J=8.7 Hz).

Example 32
tert-butylamine 2-(2,4-hexadienoyl)-7-{2-[5-methyl-2-(2,4,6-trimethylphenyl)oxazol-4-yl]ethoxy}-1,2,3,4-tetrahydroisoquinoline-(3S)-carboxylate IR $_v$ (Nujol) cm$^{-1}$; 1655, 1626, 1595, 1545, 1504.

$^1$H-NMR (CDCl$_3$) δ (ppm); 0.98 (9H, s), 1.60–2.05 (3H, m), 2.20 (6H, s), 2.29, 2.34 (6H, s, s), 2.75–3.40 (4H, m), 4.19 (2H, t, J=6.8 Hz), 4.45–5.25 (3H, m), 5.80–7.40 (12H, m).

Reference Example 1
ethyl 2-tert-butoxycarbonyl-7-hydroxy-1,2,3,4-tetrahydroisoquinoline-(3S)-carboxylate (1) 3,5-Diiodo-L-tylosin dihydrate (25 g) was suspended in conc. hydrochloric acid (250 ml), and 1,2-dimethoxyethane (18 ml) and 37% formalin (20 ml) were successively added. The mixture was heated to 75° C. over 30 min. To the reaction mixture were further added conc. hydrochloric acid (120 ml), 1,2-dimethoxyethane (9 ml) and 37% formalin (10 ml), and the mixture was stirred at 75° C. for 18 h. The precipitated crystals were collected by filtration and washed with 1,2-dimethoxyethane (20 ml) to give 7-hydroxy-6,8-diiodo-1,2,3,4-tetrahydroisoquinoline-(3S)-carboxylic acid hydrochloride (12.8 g).

IR $_v$ (Nujol) cm$^{-1}$; 1751, 1599, 1578.

$^1$H-NMR (CDCl$_3$) δ (ppm); 3.00–3.30 (2H, m), 4.05 (2H, s), 4.30 (1H, dd, J=5.9, 9.5 Hz), 7.71 (1H, s).

(2) The compound of (1) (12.8 g) was suspended in ethanol (500 ml) and conc. hydrochloric acid (10 ml) was added. The mixture was refluxed for 15 h. Ethanol was evaporated under reduced pressure, and ethyl acetate (300 ml) was added. The mixture was washed with saturated aqueous sodium hydrogen carbonate (100 ml) and saturated brine (100 ml) and dried (Na$_2$SO$_4$). Ethyl acetate was evaporated under reduced pressure to give ethyl 7-hydroxy-6,8-diiodo-1,2,3,4-tetrahydroisoquinoline-(3S)-carboxylate (11.11 g).

$^1$H-NMR (CDCl$_3$) δ (ppm); 1.29 (3H, t, J=7.0 Hz), 2.80–3.00 (2H, m), 3.30–4.10 (5H, m), 4.23 (2H, q, J=7.0 Hz), 7.46 (1H, s).

(3) 10% Pd—C (350 mg) was suspended in methanol (60 ml) and triethylamine (2.0 ml) and the compound of (2) (2.8 g) was added. The mixture was subjected to catalytic hydrogenation at room temperature at 3.0 kgf/cm$^2$ for 3 h. Pd—C was filtered off and methanol was evaporated under reduced pressure. Ethyl acetate (100 ml) was added to the obtained residue and the mixture was washed with saturated brine (100 ml) and dried (Na$_2$SO$_4$). Ethyl acetate was evaporated under reduced pressure to give ethyl 7-hydroxy-1,2,3,4-tetrahydroisoquinoline-(3S)-carboxylate (1.14 g).

IR $_v$ (Nujol) cm$^1$; 1732, 1607, 1516.

$^1$H-NMR (CDCl$_3$) δ (ppm); 1.28 (3H, t, J=7.0 Hz), 2.80–3.10 (3H, m), 3.60–3.80 (1H, m), 3.97 (2H, s), 4.05–4.20 (4H, m), 6.43 (1H, s), 6.50–6.80 (1H, m), 6.92 (1H, d, J=8.4 Hz).

(4) The compound of (3) (1.13 g) was dissolved in tetrahydrofuran (20 ml), and di-tert-butyl dicarbonate (1.5 g) was added. The mixture was stirred at room temperature for 1 h. Ethyl acetate (30 ml) was added to the reaction mixture, and the mixture was washed with saturated brine (20 ml) and dried (Na$_2$SO$_4$). Ethyl acetate was evaporated under reduced pressure and the obtained residue was purified by column chromatography to give the title compound (1.51 g).

IR $_v$ (Nujol) cm$^{-1}$; 3260, 1756, 1671, 1615, 1506.

$^1$H-NMR (CDCl$_3$) δ (ppm); 1.29 (3H, t, J=7.0 Hz), 1.47 (9H, s), 3.08 (2H, d, J=5.2 Hz), 4.21 (2H, q, J=7.0 Hz), 4.41

(1H, d, J=15.5 Hz), 4.60–5.25 (1H, m), 4.65 (1H, d, J=15.5 Hz), 5.00–6.00 (1H, br), 6.50–6.80 (2H, m), 6.98 (1H, d, J=8.1 Hz).

Reference Example 2
methyl 2-tert-butoxycarbonyl-7-hydroxy-1,2,3,4-tetrahydroisoquinoline-(3S)-carboxylate The title compound was obtained in the same manner as in Reference Example 1.

IR $_\nu$ (Nujol) cm$^{-1}$; 3261, 1755, 1672, 1614, 1506.
$^1$H-NMR (CDCl$_3$) δ (ppm); 1.47 (9H, s), 3.08 (2H, d, J=5.2 Hz), 3.63 (3H, s), 4.40 (1H, d, J=16.5 Hz), 4.60–5.25 (1H, m), 4.66 (1H, d, J=16.5 Hz), 5.60–6.60 (1H, br), 6.50–6.80 (2H, m), 6.99 (1H, d, J=8.1 Hz).

Reference Example 3
methyl 7-hydroxy-1,2,3,4-tetrahydroisoquinoline-(3S)-carboxylate The title compound was obtained in the same manner as in Reference Example 1.

IR $_\nu$ (Nujol) cm$^{-1}$; 3279, 1736, 1618, 1580.
$^1$H-NMR (CDCl$_3$) δ (ppm); 2.70–3.35 (3H, m), 3.60–3.90 (1H, m), 3.77 (3H, s), 4.03 (2H, s), 6.49 (1H, d, J=2.4 Hz), 6.64 (1H, dd, J=2.4, 7.9 Hz), 6.96 (1H, d, J=7.9 Hz).

Reference Example 4
methyl 2-(2,4-hexadienoyl)-7-hydroxy-1,2,3,4-tetrahydroisoquinoline-(3S)-carboxylate (1) Methyl 7-hydroxy-1,2,3,4-tetrahydroisoquinoline-(3S)-carboxylate (1.24 g) was dissolved in methylene chloride (25 ml), and triethylamine (5.0 ml) was added. 2,4-Hexadienoyl chloride (2.1 ml) was added dropwise to the mixture under ice-cooling. The mixture was stirred at the same temperature for 15 min, washed with 10% aqueous citric acid solution (20 ml), saturated aqueous sodium hydrogen carbonate (20 ml) and saturated brine (20 ml), and dried (Na$_2$SO$_4$). Methylene chloride was evaporated under reduced pressure and the obtained residue was purified by column chromatography. The obtained oil (1.04 g) was dissolved in methanol (20 ml), and 1M aqueous lithium hydroxide solution (3.0 ml) was added by portions at room temperature over 1 h. The mixture was acidified with 10% aqueous citric acid solution and extracted with ethyl acetate (50 ml). The ethyl acetate layer was washed with saturated brine (20 ml) and dried (Na$_2$SO$_4$). Ethyl acetate was evaporated under reduced pressure and the obtained residue was purified by column chromatography to give the title compound (0.65 g).

IR $_\nu$ (neat) cm$^{-1}$; 3184, 1734, 1576, 1506.
$^1$H-NMR (CDCl$_3$) δ (ppm); 1.84 (3H, d, J=5.0 Hz), 2.80–3.40 (2H, m), 3.59 (3H, s), 4.30–5.10 (2H, m), 5.30–5.60 (1H, m), 5.70–6.50 (4H, m), 6.64 (1H, s), 6.68 (1H, d, J=7.9 Hz), 6.99 (1H, d, J=7.9 Hz), 7.15–7.50 (1H, m).

Reference Example 5
methyl 2-(2-heptenoyl)-7-hydroxy-1,2,3,4-tetrahydroisoquinoline-(3S)-carboxylate Methyl 7-hydroxy-1,2,3,4-tetrahydroisoquinoline-(3S)-carboxylate (0.9 g) was dissolved in methylene chloride (10 ml), and 2-heptenoic acid (1.39 g) and 1-ethyl-3-(3'-dimethylaminopropyl)carbodiimide hydrochloride (2.08 g) were added. The mixture was stirred at room temperature for 30 min and methylene chloride (20 ml) was added. The mixture was washed with 10% aqueous citric acid solution (20 ml) and saturated brine (20 ml), and dried (Na$_2$SO$_4$). Methylene chloride was evaporated under reduced pressure and the obtained residue was purified by column chromatography to give the title compound (1.15 g).

IR $_\nu$ (neat) cm$^{-1}$; 3265, 1740, 1655, 1593, 1508.
$^1$H-NMR (CDCl$_3$) δ (ppm); 0.90 (3H, br-t), 1.10–1.70 (4H, m), 1.90–2.40 (2H, m), 3.00–3.40 (2H, m), 3.59 (3H, s), 4.35–5.65 (4H, m), 6.36 (1H, d, J=15.2 Hz), 6.55–6.80 (1H, m), 6.64 (1H, s), 6.80–7.20 (1H, m), 6.99 (1H, d, J=7.9 Hz).

Reference Example 6
Ethyl 7-hydroxy-2-phenyl-1,2,3,4-tetrahydroisoquinoline-3-carboxylate (1) Ethyl 4-methoxy-2-methylbenzoate (4.48 g) was dissolved in carbon tetrachloride (90 ml), and N-bromosuccinimide (4.52 g) and benzoyl peroxide (0.13 g) were added. After refluxing for h, the mixture was stirred at room temperature for 10 h. An insoluble material was filtered off and carbon tetrachloride was evaporated under reduced pressure. Ether (50 ml) was added to the residue, and the mixture was washed with 2.5M aqueous sodium hydroxide solution (30 ml) and saturated brine (50 ml), and dried (Na$_2$SO$_4$). Ether was evaporated under reduced pressure to give a powder (6.30 g).

The obtained powder (6.30 g) and N-phenylglycine ethyl ester (3.72 g) were dissolved in 2,6-lutidine (2.44 g), and the mixture was stirred at 90° C. for 2 h. After allowing to cool, water (50 ml) was added, and the mixture was extracted twice with ethyl acetate (30 ml). The ethyl acetate layers were combined and washed with 1M hydrochloric acid (30 ml) and saturated brine (50 ml), and dried (Na$_2$SO$_4$). Ethyl acetate was evaporated under reduced pressure and the obtained residue was purified by column chromatography to give ethyl 2-[(ethoxycarbonylmethyl-phenyl-amino)methyl]-4-methoxybenzoate (4.16 g).

IR $_\nu$ (neat) cm$^{-1}$; 1747, 1707, 1605, 1506, 1261, 1184, 1128, 1036, 750, 692.
$^1$H-NMR (CDCl$_3$) δ (ppm); 1.26 (3H, t, J=7.1 Hz), 1.38 (3H, t, J=7.1 Hz), 3.74 (3H, s), 4.11 (2H, s), 4.21 (2H, q, J=7.1 Hz), 4.33 (2H, q, J=7.1 Hz), 5.01 (2H, s), 6.5–6.9 (4H, m), 7.0–7.3 (3H, m), 8.04 (1H, d, J=8.6 Hz).

(2) The compound of (1) (4.11 g) was dissolved in benzene (250 ml), and sodium hydride (60% oil suspension, 1.77 g) was added. The mixture was stirred for 15 min and ethanol (0.25 ml) was added. The mixture was further refluxed for 6 h and excess sodium hydride was neutralized with acetic acid. The reaction mixture was washed with 5% aqueous citric acid solution (50 ml), saturated aqueous sodium hydrogen carbonate solution (50 ml) and saturated brine (50 ml), and dried (Na$_2$SO$_4$). Benzene was evaporated under reduced pressure and the obtained residue was purified by column chromatography to give ethyl 7-methoxy-4-oxo-2-phenyl-1,2,3,4-tetrahydroisoquinoline-3-carboxylate (2.39 g).

IR $_\nu$ (Nujol) cm$^{-1}$; 1641, 1611, 1556, 1327, 1283, 1248, 1101, 1018, 822, 762.
$^1$H-NMR (CDCl$_3$) δ (ppm); 1.09 (3H, t, J=7.1 Hz), 3.77 (3H, s), 4.20 (2H, q, J=7.1 Hz), 4.24 (2H, s), 5.19, 11.86 (1H, s, s), 6.5–7.4 (7H, m), 7.71, 8.06 (1H, d, d, J=8.6, 8.6 Hz).

(3) The compound of (2) (500 mg) was suspended in ethanol (10 ml) and sodium borohydride (58 mg) was added under ice-cooling. The mixture was stirred for 20 min and further stirred at room temperature for 3 h. Ethanol was evaporated under reduced pressure, and 1M hydrochloric acid (10 ml) was added. The mixture was extracted with ethyl acetate (30 ml) and the ethyl acetate layer was washed with saturated brine (20 ml), and dried (Na$_2$SO$_4$). Ethyl acetate was evaporated under reduced pressure and the obtained residue purified by column chromatography to give ethyl 4-hydroxy-7-methoxy-2-phenyl-1,2,3,4-tetrahydroisoquinoline-3-carboxylate (490 mg).

IR $_v$ (neat) cm$^{-1}$; 3800–3200, 1732, 1599, 1504, 1462, 1381, 1277, 752, 692.

$^1$H-NMR (CDCl$_3$) δ (ppm); 0.98 (3H, t, J=7.0 Hz), 3.80 (3H, s) 3.9–4.2 (2H, m), 4.2–4.7 (2H, m), 4.8–5.2 (2H, m), 6.6–7.0 (5H, m), 7.2–7.5 (2H, m), 7.59 (1H, d, J=8.4 Hz).

(4) 10% Pd—C (wet) (150 mg) was suspended in acetic acid (10 ml) and the compound of (3) (490 mg) and conc. hydrochloric acid (1.0 ml) were added. The mixture was subjected to hydrogenation at 40° C. and 4 kgf/cm$^2$ for 6 h. Pd—C was filtered off and acetic acid was evaporated under reduced pressure. The residue was neutralized with saturated aqueous sodium hydrogen carbonate solution. The mixture was extracted with ethyl acetate (20 ml), and the ethyl acetate layer was washed with saturated aqueous sodium hydrogen carbonate solution (100 ml) and saturated brine (100 ml), and dried (Na$_2$SO$_4$). Ethyl acetate was evaporated under reduced pressure and the obtained residue was purified by column chromatography to give ethyl 7-methoxy-2-phenyl-1,2,3,4-tetrahydroisoquinoline-3-carboxylate (205 mg).

$^1$H-NMR (CDCl$_3$) δ (ppm); 1.03 (3H, t, J=7.0 Hz), 3.25 (2H, d, J=4.4 Hz), 3.79 (3H, s), 3.99 (2H, q, J=7.0 Hz), 4.56 (2H, s), 4.76 (1H, t, J=4.4 Hz), 6.6–7.4 (8H, m).

(5) The compound of (4) (205 mg) was dissolved in methylene chloride (4 ml), and boron tribromide (0.12 ml) was added at a temperature of not higher than −10° C. The mixture was stirred at room temperature for 1.5 h. Methylene chloride (20 ml) and 2M hydrochloric acid (10 ml) were added under ice-cooling, and two layers were separated. The methylene chloride layer was washed with saturated aqueous sodium hydrogen carbonate solution (20 ml) and then saturated brine (20 ml), and dried (Na$_2$SO$_4$). Methylene chloride was evaporated under reduced pressure and the obtained residue was purified by column chromatography to give the title compound (100 mg).

$^1$H-NMR (CDCl$_3$) δ (ppm); 1.05 (3H, t, J=7.1 Hz), 3.23 (2H, d, J=4.1 Hz), 4.01 (2H, q, J=7.1 Hz), 4.50 (2H, s), 4.75 (1H, t, J=4.1 Hz), 5.01 (1H, br-s), 6.6–7.5 (8H, m).

Reference Example 7

2-(5-methyl-2-phenyloxazol-4-yl)ethyl methanesulfonate 2-(5-Methyl-2-phenyloxazol-4-yl)ethanol (20 g) and triethylamine (19.2 ml) were added to methylene chloride (200 ml) and, after dropwise addition of methanesulfonyl chloride (9.52 ml) at 0° C., the mixture was stirred at the same temperature for 15 min. The reaction mixture was washed with 10% aqueous citric acid solution (200 ml), saturated aqueous sodium hydrogen carbonate solution (100 ml) and saturated brine (100 ml), and dried (Na$_2$SO$_4$). Methylene chloride was evaporated under reduced pressure and the obtained residue was purified by column chromatography to give the title compound (21.45 g). $^1$H-NMR (CDCl$_3$) δ (ppm); 2.53 (3H, s), 2.94 (3H, s), 2.94 (2H, t, J=7.0 Hz), 4.52 (2H, t, J=7.0 Hz), 7.30–7.50 (3H, m), 7.80–8.10 (2H, m).

Reference Example 8

2-[2-(4-isopropylphenyl)-5-methyloxazol-4-yl]ethyl methanesulfonate (1) 4-Isopropylbenzamide (20.8 g) was suspended in toluene (70 ml) and methyl 4-bromopropionylacetate (24.2 g) was added. The mixture was refluxed for 14 h. An insoluble material was filtered off and ethyl acetate (50 ml) was added. The mixture was washed successively with water (50 ml) and saturated brine (50 ml), and dried (Na$_2$SO$_4$). The solvent was evaporated under reduced pressure and the residue was purified by column chromatography. Isopropyl ether was added to the obtained crystalline residue and the mixture was filtrated to give methyl 2-[2-(4-isopropylphenyl)-5-methyloxazol-4-yl]acetate (6.57 g).

IR $_v$ (neat) cm$^{-1}$; 1744, 1643, 1614, 1582, 1556.

$^1$H-NMR (CDCl$_3$) δ (ppm); 1.26 (6H, d, J=6.8 Hz), 2.34 (3H, s), 2.93 (1H, heptet, J=6.8 Hz), 3.56 (2H, s), 3.71 (3H, s), 7.26, 7.90 (4H, ABq, J=8.3 Hz).

(2) The compound of (1) (6.5 g) was dissolved in tetrahydrofuran (130 ml) and lithium aluminum hydride (0.9 g) as added by portions at 0° C. The mixture was stirred at the same temperature for 30 min. Ethyl acetate (100 ml) and water (50 ml) were added. An insoluble material was filtered off and two layers were separated. The ethyl acetate layer was washed successively with water (100 ml) and saturated brine (70 ml), and dried (Na$_2$SO$_4$). Ethyl acetate was evaporated under reduced pressure and a mixture of n-hexane-isopropyl ether (1:1) was added to the obtained crystalline residue. Filtration gave 2-[2-(4-isopropylphenyl)-5-methyloxazol-4-yl]ethanol (3.25 g).

IR $_v$ (neat) cm$^{-1}$; 3088, 1697, 1508.

$^1$H-NMR (CDCl$_3$) δ (ppm); 1.26 (6H, d, J=7.0 Hz), 2.28 (3H, s) 2.69 (2H, t, J=5.9 Hz), 2.93 (1H, heptet, J=6.8 Hz)., 3.54 (1H, br-s), 3.91 (2H, t, J=5.9 Hz), 7.22, 7.87 (4H, ABq, J=8.3 Hz).

(3) The compound of (2) (3.22 g) and triethylamine (2.75 ml) were added to methylene chloride (30 ml) and methanesulfonyl chloride (1.11 ml) was dropwise added at 0° C. The mixture was stirred at the same temperature for 20 min. Methylene chloride (30 ml) was added, and the mixture was washed successively with 10% aqueous citric acid solution (30 ml) and saturated brine (30 ml), and dried (Na$_2$SO$_4$). Methylene chloride was evaporated under reduced pressure and a mixture of n-hexane-isopropyl ether (1:1) was added to the obtained crystalline residue. Filtration gave the title compound (3.63 g).

IR $_v$ (Nujol) cm$^{-1}$; 1643, 1614, 1582, 1556, 1506.

$^1$H-NMR (CDCl$_3$) δ (ppm); 1.27 (6H, d, J=6.8 Hz), 2.34 (3H, s), 2.70–3.20 (3H, m), 2.94 (3H, br-s), 4.51 (2H, t, J=6.6 Hz), 7.28, 7.88 (4H, ABq, J=8.3 Hz).

The following compounds were synthesized in the same manner as in Reference Example 8.

Reference Example 9

2-[2-(4-tert-butylphenyl)-5-methyloxazol-4-yl]ethyl methanesulfonate

IR $_v$ (Nujol) cm$^{-1}$; 1643, 1497.

$^1$H-NMR (CDCl$_3$) δ (ppm); 1.34 (9H, s), 2.34 (3H, s), 2.93 (3H, s), 2.93 (2H, t, J=6.0 Hz), 4.51 (2H, t, J=6.0 Hz), 7.44, 7.88 (4H, ABq, J=8.6 Hz).

Reference Example 10

2-[5-methyl-2-(4-trifluoromethylphenyl)oxazol-4-yl]ethyl methanesulfonate

IR $_v$ (Nujol) cm$^{-1}$; 1620.

$^1$H-NMR (CDCl$_3$) δ (ppm); 2.38 (3H, s), 2.96 (2H, t, J=6.5 Hz), 2.96 (3H, s), 4.53 (2H, t, J=6.5 Hz), 7.68, 8.08 (4H, ABq, J=8.3 Hz).

Reference Example 11

2-[2-(4-fluorophenyl)-5-methyloxazol-4-yl]ethyl methanesulfonate

IR $_v$ (Nujol) cm$^{-1}$; 1636, 1603, 1560, 1499.

$^1$H-NMR (CDCl$_3$) δ (ppm); 2.33 (3H, s), 2.92 (2H, t, J=6.6 Hz), 2.94 (3H, s), 3.85 (3H, s), 4.51 (2H, t, J=6.6 Hz), 6.94, 7.89 (4H, ABq, J=8.7 Hz).

Reference Example 12
2-[2-(4-methoxyphenyl)-5-methyloxazol-4-yl]ethyl methanesulfonate IR $_\nu$ (Nujol) cm$^{-1}$; 1643, 1611, 1587.

$^1$H-NMR (CDCl$_3$) δ (ppm); 2.33 (3H, s), 2.92 (2H, t, J=6.6 Hz), 2.94 (3H, s), 3.85 (3H, s), 4.51-(2H, t, J=6.6 Hz), 6.94, 7.89 (4H, ABq, J=8.7 Hz).

Reference Example 13
2-[5-methyl-2-(p-tolyl)oxazol-4-yl]ethyl methanesulfonate IR $_\nu$ (Nujol) cm$^{-1}$; 1634, 1616, 1582, 1556, 1501.

$^1$H-NMR (CDCl$_3$) δ (ppm); 2.34 (3H, s), 2.39 (3H, s), 2.93 (2H, t, J=6.6 Hz), 2.94 (3H, s), 4.52 (2H, t, J=6.6 Hz), 7.23, 7.85 (4H, ABq, J=8.1 Hz).

Reference Example 14
2-[2-(4-chlorophenyl)-5-methyloxazol-4-yl]ethyl ethanesulfonate IR $_\nu$ (Nujol) cm$^{-1}$; 3400, 3090, 3034, 1643, 1605, 1582, 1551.

$^1$H-NMR (CDCl$_3$) δ (ppm); 2.35 (3H, s), 2.94 (2H, t, J=6.5 Hz), 2.96 (3H, s), 4.51 (2H, t, J=6.5 Hz), 7.40, 7.90 (4H, ABq, J=8.6 Hz).

Reference Example 15
2-[2-(3,4-dimethoxyphenyl)-5-methyloxazol-4-yl]ethyl methanesulfonate IR $_\nu$ (Nujol) cm$^{-1}$; 1645, 1609, 1589, 1564, 1510.

$^1$H-NMR (CDCl$_3$) δ (ppm); 2.35 (3H, s), 2.93 (2H, t, J=6.6 Hz), 2.95 (3H, s), 3.92, 3.96 (6H, s, s), 4.52 (2H, t, J=6.6 Hz), 6.91 (1H, d, J=7.9 Hz), 7.45–7.70 (2H, m).

Reference Example 16
2-[2-(3,4-methylenedioxyphenyl)-5-methyloxazol-4-yl]ethyl methanesulfonate IR $_\nu$ (Nujol) cm$^{-1}$; 1637, 1608, 1566, 1560, 1504.

$^1$H-NMR (CDCl$_3$) δ (ppm); 2.33 (3H, s), 2.92 (2H, t, J=6.7 Hz), 2.95 (3H, s), 4.51 (2H, t, J=6.7 Hz), 6.01 (2H, s), 6.85 (1H, d, J=8.1 Hz), 7.35–7.65 (2H, m).

Reference Example 17
2-[5-methyl-2-(o-tolyl)oxazol-4-yl]ethyl methanesulfonate IR $_\nu$ (neat) cm$^{-1}$; 1645, 1607, 1580, 1549.

$^1$H-NMR (CDCl$_3$) δ (ppm); 2.35 (3H, s), 2.65 (3H, s), 2.94 (3H, br), 2.95 (2H, t, J=6.6 Hz), 4.53 (2H, q, J=6.6 Hz), 7.15–7.45 (3H, m), 7.80–8.05 (1H, m).

Reference Example 18
2-[2-(4-benzyloxyphenyl)-5-methyloxazol-4-yl]ethyl methanesulfonate IR $_\nu$ (Nujol) cm$^{-1}$; 1643, 1614, 1587, 1500.

$^1$H-NMR (CDCl$_3$) δ (ppm); 2.31 (3H, s), 2.91 (3H, s), 2.92 (2H, t, J=6.7 Hz), 4.49 (2H, J=6.7 Hz), 5.08 (2H, s), 7.38 (5H, br-s), 6.99, 7.88 (1H, ABq, J=8.6 Hz).

Reference Example 19
2-[2-(2,4-dimethylphenyl)-5-methyloxazol-4-yl]ethyl methanesulfonate IR $_\nu$ (neat) cm$^{-1}$; 3018, 2924, 2862, 1645, 1616, 1576, 1553, 1493.

$^1$H-NMR (CDCl$_3$) δ (ppm); 2.34 (6H, s), 2.60 (3H, s), 2.94 (3H, s), 2.94 (2H, t, J=6.6 Hz), 4.53 (2H, J=6.6 Hz), 6.95–7.20 (2H, m), 7.79 (1H, d, J=8.4 Hz)

Reference Example 20
2-[5-methyl-2-(4-nitrophenyl)oxazol-4-yl]ethyl methanesulfonate IR $_\nu$ (Nujol) cm$^{-1}$; 1638, 1601, 1553, 1522.

$^1$H-NMR (CDCl$_3$) δ (ppm); 2.40 (3H, s), 2.98 (3H, s), 2.98 (2H, t, J=6.4 Hz), 4.53 (2H, t, J=6.4 Hz), 8.11, 8.30 (4H, ABq, J=9.0 Hz).

Reference Example 21
2-[2-(4-dimethylaminophenyl)-5-methyloxazol-4-yl]ethyl methanesulfonate

Reference Example 22
2-[5-methyl-2-(2,4,6-trimethylphenyl)oxazol-4-yl]ethyl methanesulfonate IR $_\nu$ (neat) cm$^{-1}$; 1645, 1609, 1589, 1564, 1510.

$^1$H-NMR (CDCl$_3$) δ (ppm); 2.20 (6H, s), 2.30, 2.33 (6H, s, s), 2.96 (2H, t, J=6.6 Hz), 2.96 (3H, s), 4.52 (2H, t, J=6.6 Hz), 6.90 (2H, s).

Experimental Example 1

Using male KK-A$^y$ mice, which were spontaneously diabetic models, which had developed diabetes due to insulin resistance, and which showed high plasma glucose, hypertriglyceridemia and hyperinsulinemia, the pharmacological activity of the test compounds was examined.

Test Method

Blood was drawn under a non-fasting state from the tail vein of male KK-A$^y$ mice, and the glucose and triglyceride levels of the plasma were measured using commercially available assay kits (glucose CII-test WAKO and triglyceride G-test WAKO, Wako Pure Chemical Industries, Ltd.). The mice were grouped (5 mice per group) into a control group and an administration group, such that the mean and standard deviation of the body weight and the plasma glucose and plasma triglyceride levels in each group were nearly the same. The test compounds (compounds of Examples 2, 6, 8, 16, 26, 27 and 31) were suspended in 5% gum arabic solution and administered (10 mg/kg/day) orally to the administration group for 4 consecutive days from the next day. The 5% gum arabic solution was orally administered to the control group. Blood was drawn under a non-fasting state from the tail vein 24 hours after the final administration and the glucose and triglyceride levels of the plasma were measured. The decrease in the plasma glucose and triglyceride levels was calculated from the following formula. The results are shown in Table 1.

Decrease (%)=[(mean of control group−mean of test compound administration group)/mean of control group]×100

Results

TABLE 1

| Test compound | Decrease (%) in glucose level | Decrease (%) in triglyceride |
|---|---|---|
| Example 2 | 46.8 | 44.9 |
| Example 6 | 45.9 | 45.7 |
| Example 8 | 46.1 | 55.2 |
| Example 16 | 60.9 | 73.4 |
| Example 26 | 43.7 | 67.8 |
| Example 27 | 55.8 | 73.8 |
| Example 31 | 39.4 | 20.1 |

Experimental Example 2

Using db/db mice genetically showing high plasma glucose, hypertriglyceridemia, insulin resistance andobesity, the pharmacological activity of the test compound of Example 6 was examined.

Test Method

Blood was drawn under a non-fasting state from the tail vein of male db/db mice, the glucose level and triglyceride level of the plasma were measured using commercially available assay kits (glucose CII-test WAKO and triglyceride G-test WAKO, Wako Pure Chemical Industries, Ltd.). The mice were grouped (6 mice per group) into a control group and test compound (compound of Example 6) administration groups (3 and 10 mg/kg/day), such that the mean and standard deviation of the body weight and the plasma glucose and plasma triglyceride levels in each group were nearly the same. The test compound was suspended in 0.5% methylcellulose solution and administered orally for 2 consecutive weeks from the next day. The 0.5% methylcellulose solution was orally administered to the control group. Blood was drawn under a non-fasting state from the tail vein 24 hours after the final administration and the glucose and triglyceride levels of the plasma were measured. The decrease in the plasma glucose and triglyceride levels was calculated from the following formula. The results are shown in Table 2.

Decrease (%)=[(mean of control group−mean of test compound administration group)/mean of control group]×100

Results

TABLE 2

| Dose | Decrease (%) in glucose level | Decrease (%) in triglyceride |
|---|---|---|
| 3 mg/kg/day | 59.9 | 77.1 |
| 10 mg/kg/day | 64.4 | 78.8 |

The test compound (compound of Example 6) decreased the plasma glucose and triglyceride levels to almost the normal levels at the dose of 3 and 10 mg/kg/day.

Experimental Example 3

Using 6-week-old male SD rats, toxicity by repeat administration was examined.

Test Method

The rats were grouped (6 rats per group) into a control group and test compound (compound of Example 6) administration groups (30 and 100 mg/kg/day), such that the mean and standard deviation of the body weight of the rats were nearly the same. The test compound was suspended in 0.5% methylcellulose solution and administered orally for 4 consecutive weeks from the next day. The 0.5% methylcellulose solution was orally administered to the control group. The rats were fasted for 16 hr from the last day of administration, anesthetized by intraperitoneal administration of pentobarbital sodium (50 mg/kg) 24 hr after the final administration and the blood was drawn. Using EDTA-added blood, hematocrit value and erythrocyte count were measured, and using serum, AST (GOT) and ALT (GPT) were measured. In addition, the total blood volume was calculated. The white fat around the epididymides, and the liver and heart were removed and wet weights thereof were measured.

Results

There was found no significant difference in the body weight, total blood volume, hematocrit value, erythrocyte count, weights of white fat around the epididymides, and the liver and heart, and AST (GOT) and ALT (GPT) of the test compound (compound of Example 6) administration (30 and 100 mg/kg/day) group from those of the control group.

Experimental Example 4

Using 6-week-old female Wistar rats, toxicity by repeat administration was examined.

Test Method

The rats were grouped (6 rats per group) into a control group and test compound (compound of Example 6) administration groups (30 and 100 mg/kg/day), such that the mean and the standard deviation of the body weight of the rats were nearly the same. The test compound was suspended in 0.5% methylcellulose solution and administered orally for 2 consecutive weeks from the next day. The 0.5% methylcellulose solution was orally administered to the control group. The rats were fasted for 16 hr from the last day of administration, anesthetized by intraperitoneal administration of pentobarbital sodium (50 mg/kg) 24 hr after the final administration and the blood was drawn. Using EDTA-added blood, hematocrit value and erythrocyte count were measured, and using serum, AST (GOT) and ALT (GPT) were measured. In addition, the total blood volume was calculated. The white fat around the uterus, and the liver and heart were removed and wet weights thereof were measured.

Results

There was found no significant difference in the body weight, total blood volume, hematocrit value, erythrocyte count, weight of white fat around the uterus, and the liver and heart, AST (GOT) and ALT (GPT) of the test compound (compound of Example 6) administration (30 and 100 mg/kg/day) group from those of the control group.

INDUSTRIAL APPLICABILITY

The novel heterocyclic derivative having the above-mentioned formula (I') of the present invention and a pharmaceutically acceptable salt thereof have a hypoglycemic action, a blood hypolipidemic action, an insulin resistance improving action and a PPAR activating action, and are useful as a hypoglycemic agent, a hypolipidemic agent, an insulin resistance improver, a therapeutic agent of diabetes, a therapeutic agent of diabetic complications, a glucose intolerance improver, an anti-arteriosclerosis agent, an anti-obesity agent, an antiinflammatory agent, an agent for the prophylaxis or treatment of PPAR-mediated diseases and an agent for the prophylaxis or treatment of syndrome X.

This application is based on patent application No. 2001-161488 filed in Japan, the contents of which are hereby incorporated by reference.

What is claimed is:

1. A novel heterocyclic derivative of the formula (I')

(I')

wherein
R$^1$ is a hydrogen atom or $C_{1-6}$ alkyl,
R$^2$ is —CO—C(R$^4$)=C(R$^4$)—R$^5$ wherein R$^4$ is a hydrogen atom or $C_{1-4}$ alkyl, and R$^5$ is $C_{4-8}$ alkyl, $C_{2-8}$ alkenyl, aryl or aromatic heterocycle, —CO—C≡C—R$^6$ wherein R$^6$ is $C_{1-8}$ alkyl, —CO—CO—R$^7$ wherein R$^7$ is $C_{1-8}$ alkyl or $C_{1-8}$ alkoxy, —N(R$^8$)—CO—R$^9$ wherein R$^8$ is a hydrogen atom or $C_{1-4}$ alkyl, and R$^9$ is $C_{1-8}$alkyl, $C_{1-8}$ alkoxy, aryl or aryl $C_{1-3}$ alkoxy, or aryl, R³ is a hydrogen atom or C_{1-4} alkyl, X is an oxygen atom or a sulfur atom, R²⁰ is optionally substituted phenyl, and n is an integer of 1 to 4, or a pharmaceutically acceptable salt thereof.

2. A novel heterocyclic derivative of the formula (I)

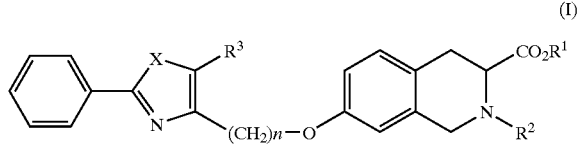

(I)

wherein

R¹ is a hydrogen atom or C_{1-6} alkyl,

R² is —CO—C(R⁴)═C(R⁴)—R⁵ wherein R⁴ is a hydrogen atom or C_{1-4} alkyl, and R⁵ is C_{4-8} alkyl, C_{2-8} alkenyl, aryl or aromatic heterocycle, —CO—C═C—R⁶ wherein R⁶ is C_{1-8} alkyl, —CO—CO—R⁷ wherein R⁷ is C_{1-8} alkyl or C_{1-8} alkoxy, —N(R)—CO—R⁹ wherein R⁸ is a hydrogen atom or C_{1-4} alkyl, and R⁹ is C_{1-8} alkyl, C_{1-8} alkoxy, aryl or aryl C_{1-3} alkoxy, or aryl, R³ is a hydrogen atom or C_{1-4} alkyl, X is an oxygen atom or a sulfur atom, and n is an integer of 1 to 4, or a pharmaceutically acceptable salt thereof.

3. The novel heterocyclic derivative of claim 2, wherein, in the formula (I), R¹ is a hydrogen atom, R³ is a hydrogen atom or methyl, X is an oxygen atom, and n is 2, or a pharmaceutically acceptable salt thereof.

4. The novel heterocyclic derivative of claim 3, wherein, in the formula (I), R² is —CO—C(R⁴)═C(R⁴)—R⁵ wherein R⁴ is a hydrogen atom or C_{1-4} alkyl and R⁵ is C_{4-8} alkyl, C_{2-8} alkenyl or aryl, or a pharmaceutically acceptable salt thereof.

5. The novel heterocyclic derivative of claim 3, wherein, in the formula (I), R² is —CO—C≡C—R⁶ wherein R⁶ is C_{1-8} alkyl, or a pharmaceutically acceptable salt thereof.

6. The novel heterocyclic derivative of claim 4, wherein, in the formula (I), R² is —CO—C(R⁴)═C(R⁴)—R⁵ wherein R⁴ is a hydrogen atom and R⁵ is C_{4-8} alkyl or C_{2-8} alkenyl, or a pharmaceutically acceptable salt thereof.

7. The heterocyclic derivative of claim 2, wherein the derivative of the formula (I) is any of the following [1] to [12], or a pharmaceutically acceptable salt thereof:

[1] 2-(2,4-hexadienoyl)-7-[2-(5-methyl-2-phenyloxazol-4-yl)ethoxy]-1,2,3,4-tetrahydroisoquinoline-(3S)-carboxylic acid,

[2] 2-(2-heptenoyl)-7-[2-(5-methyl-2-phenyloxazol-4-yl)ethoxy]-1,2,3,4-tetrahydroisoquinoline-(3S)-carboxylic acid,

[3] 7-[2-(5-methyl-2-phenyloxazol-4-yl)ethoxy]-2-(2,4-octadienoyl)-1,2,3,4-tetrahydroisoquinoline-(3S)-carboxylic acid,

[4] 2-(2-hexynoyl)-7-[2-(5-methyl-2-phenyloxazol-4-yl)ethoxy]-1,2,3,4-tetrahydroisoquinoline-(3S)-carboxylic acid,

[5] 2-cinnamoyl-7-[2-(5-methyl-2-phenyloxazol-4-yl)ethoxy]-1,2,3,4-tetrahydroisoquinoline-(3S)-carboxylic acid,

[6] 7-[2-(5-methyl-2-phenyloxazol-4-yl)ethoxy]-2-(2-oxo-butyryl)-1,2,3,4-tetrahydroisoquinoline-(3S)-carboxylic acid,

[7] 2-ethoxyoxalyl-7-[2-(5-methyl-2-phenyloxazol-4-yl)ethoxy]-1,2,3,4-tetrahydroisoquinoline-(3S)-carboxylic acid,

[8] 7-[2-(5-methyl-2-phenyloxazol-4-yl)ethoxy]-2-(2-octenoyl)-1,2,3,4-tetrahydroisoquinoline-(3S)-carboxylic acid,

[9] 2-benzoylamino-7-[2-(5-methyl-2-phenyloxazol-4-yl)ethoxy]-1,2,3,4-tetrahydroisoquinoline-(3S)-carboxylic acid,

[10] 2-(2,2-dimethylpropionylamino)-7-[2-(5-methyl-2-phenyloxazol-4-yl)ethoxy]-1,2,3,4-tetrahydroisoquinoline-(3S)-carboxylic acid,

[11] 2-tert-butoxycarbonylamino-7-[2-(5-methyl-2-phenyloxazol-4-yl)ethoxy]-1,2,3,4-tetrahydroisoquinoline-(3S)-carboxylic acid, and

[12] 7-[2-(5-methyl-2-phenyloxazol-4-yl)ethoxy]-2-phenyl-1,2,3,4-tetrahydroisoquinoline-(3RS)-carboxylic acid.

8. A pharmaceutical composition containing the novel heterocyclic derivative of any of claims 2 to 7, or a pharmaceutically acceptable salt thereof.

9. A pharmaceutical agent containing the novel heterocyclic derivative of any of claims 2 to 7, or a pharmaceutically acceptable salt thereof, which is selected from the group consisting of a hypoglycemic agent, a hypolipidemic agent, an insulin resistance improver, a therapeutic agent of diabetes, a therapeutic agent of diabetic complications, a glucose intolerance improver, an anti-arteriosclerosis agent, an anti-obesity agent, an antiinflammatory agent, an agent for the prophylaxis or treatment of PPAR-mediated diseases and an agent for the prophylaxis or treatment of syndrome X.

10. The heterocyclic derivative of claim 1, wherein the derivative of the formula (I') is any of the following [13] to [29], or a pharmaceutically acceptable salt thereof:

[13] 7-{2-[2-(4-tert-butylphenyl)-5-methyloxazol-4-yl]ethoxy}-2-(2,4-hexadienoyl)-1,2,3,4-tetrahydroisoquinoline-(3S)-carboxylic acid,

[14] 2-(2,4-hexadienoyl)-7-{2-[5-methyl-2-(4-trifluoromethylphenyl)oxazol-4-yl]ethoxy}-1,2,3,4-tetrahydroisoquinoline-(3S)-carboxylic acid,

[15] 7-{2-[2-(4-fluorophenyl)-5-methyloxazol-4-yl]ethoxy}-2-(2,4-hexadienoyl)-1,2,3,4-tetrahydroisoquinoline-(3S)-carboxylic acid,

[16] 2-(2,4-hexadienoyl)-7-{2-[2-(4-methoxyphenyl)-5-methyloxazol-4-yl]ethoxy}-1,2,3,4-tetrahydroisoquinoline-(3S)-carboxylic acid,

[17] 2-(2,4-hexadienoyl)-7-{2-[5-methyl-2-(p-tolyl)oxazol-4-yl]ethoxy}-1',2,3,4-tetrahydroisoquinoline-(3S)-carboxylic acid,

[18] 7-{2-[2-(4-chlorophenyl)-5-methyloxazol-4-yl]ethoxy}-2-(2,4-hexadienoyl)-1,2,3,4-tetrahydroisoquinoline-(3S)-carboxylic acid,

[19] 7-{2-[2-(3,4-dimethoxyphenyl)-5-methyloxazol-4-yl]ethoxy}-2-(2,4-hexadienoyl)-1,2,3,4-tetrahydroisoquinoline-(3S)-carboxylic acid,

[20] 7-{2-[2-(3,4-methylenedioxyphenyl)-5-methyloxazol-4-yl]ethoxy}-2-(2,4-hexadienoyl)-1,2,3,4-tetrahydroisoquinoline-(3S)-carboxylic acid,

[21] 2-(2,4-hexadienoyl)-7-{2-[2-(4-hydroxyphenyl)-5-methyloxazol-4-yl]ethoxy}-1,2,3,4-tetrahydroisoquinoline-(3S)-carboxylic acid,

[22] 2-(2,4-hexadienoyl)-7-{2-[5-methyl-2-(o-tolyl)oxazol-4-yl]ethoxy}-1,2,3,4-tetrahydroisoquinoline-(3S)-carboxylic acid,

[23] 7-{2-[2-(4-benzyloxyphenyl)-5-methyloxazol-4-yl]ethoxy}-2-(2,4-hexadienoyl)-1,2,3,4-tetrahydroisoquinoline-(3S)-carboxylic acid,

[24] 2-(2,4-hexadienoyl)-7-{2-[2-(4-isopropylphenyl)-5-methyloxazol-4-yl]ethoxy}-1,2,3,4-tetrahydroisoquinoline-(3S)-carboxylic acid,

[25] 7-{2-[2-(2,4-dimethylphenyl)-5-methyloxazol-4-yl]ethoxy}-2-(2,4-hexadienoyl)-1,2,3,4-tetrahydroisoquinoline-(3S)-carboxylic acid,

[26] 2-(2,4-hexadienoyl)-7-{2-[5-methyl-2-(4-nitrophenyl)-oxazol-4-yl]ethoxy}-1,2,3,4-tetrahydroisoquinoline-(3S)-carboxylic acid,

[27] 7-{2-[2-(4-aminophenyl)-5-methyloxazol-4-yl]ethoxy}-2-(2,4-hexadienoyl)-1,2,3,4-tetrahydroisoquinoline-(3S)-carboxylic acid,

[28] 7-{2-[2-(4-dimethylaminophenyl)-5-methyloxazol-4-yl]ethoxy}-2-(2,4-hexadienoyl)-1,2,3,4-tetrahydroisoquinoline-(3S)-carboxylic acid, and

[29] 2-(2,4-hexadienoyl)-7-{2-[5-methyl-2-(2,4,6-trimethylphenyl)oxazol-4-yl]ethoxy}-1,2,3,4-tetrahydroisoquinoline-(3S)-carboxylic acid.

11. A pharmaceutical composition comprising the novel heterocyclic derivative of claim 1 or 10, or a pharmaceutically acceptable salt thereof.

12. A pharmaceutical agent containing the novel heterocyclic derivative of claim 1 or 10, or a pharmaceutically acceptable salt thereof, which is selected from the group consisting of a hypoglycemic agent, a hypolipidemic agent, an insulin resistance improver, a therapeutic agent of diabetes, a therapeutic agent of diabetic complications, a glucose intolerance improver, an anti-arteriosclerosis agent, an anti-obesity agent, an antiinflammatory agent, an agent for the prophylaxis or treatment of PPAR-mediated diseases and an agent for the prophylaxis or treatment of syndrome X.

* * * * *